(12) United States Patent
Amrad et al.

(10) Patent No.: US 10,750,701 B2
(45) Date of Patent: Aug. 25, 2020

(54) VERNALIZATION INDEPENDENT LISIANTHUS PLANTS

(71) Applicant: Yissum Research Development Company of the Hebrew University of Jerusalem Ltd., Jerusalem (IL)

(72) Inventors: Avichai Amrad, D.N. Merom Hagalil Mitzpe Amuka (IL); Kfir Bandel, Rehovot (IL); Tzili Pleban, Kiryat ono (IL); Dani Zamir, Gedera (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 193 days.

(21) Appl. No.: 15/529,320

(22) PCT Filed: Nov. 24, 2015

(86) PCT No.: PCT/IL2015/051140
§ 371 (c)(1),
(2) Date: May 24, 2017

(87) PCT Pub. No.: WO2016/084077
PCT Pub. Date: Jun. 2, 2016

(65) Prior Publication Data
US 2017/0258023 A1 Sep. 14, 2017

Related U.S. Application Data

(60) Provisional application No. 62/083,912, filed on Nov. 25, 2014.

(51) Int. Cl.
*A01H 6/40* (2018.01)
*A01H 1/04* (2006.01)
(52) U.S. Cl.
CPC ............... *A01H 6/40* (2018.05); *A01H 1/04* (2013.01)
(58) Field of Classification Search
CPC ....................................................... A01H 6/40
See application file for complete search history.

(56) References Cited

FOREIGN PATENT DOCUMENTS

WO 2009/126573 A2 10/2009
WO 2010143749 A1 12/2010

OTHER PUBLICATIONS

Turner Phytologia vol. 96, No. 1, pp. 7-11 (Year: 2014).*
Harbaugh Flower Breeding and Genetics, Chapter 24, pp. 645-664 Anderson, editor Springer, Dordrecht, The Neatherlands (Year: 2007).*
Harbaugh et al HortScience vol. 33, issue 1, pp. 164-165 (Year: 1998).*
Barba-Gonzalez et al Acta Horticulturae No. 1171, pp. 241-244 (Year: 2017).*
Deng et al., (2011) Flowering Locus C (FLC) regulates development pathways throughout the life cycle of Arabidopsis. Proceedings of the National Academy of Sciences, 108(16), 6680-6685.
Ecker et al., (1993) Quantitative genetic analysis of growth rate in lisianthus. Plant Breed 111: 253-256.
Ecker et al., (1994) Inheritance of seed dormancy in lisianthus (*Eustoma grandiflorum*). Plant breeding, 113(4), 335-338.
Ecker et al., (1994) Population means and correlation analyses of growth parameters in lisianthus (*Eustoma grandiflorum* Shinn.). Euphytica, 78(3), 193-197.
Elshire et al., (2011) A robust, simple genotyping-by-sequencing (GBS) approach for high diversity species. PloS one, 6(5), e19379.
Fulton et al., (1995) Microprep protocol for extraction of DNA from tomato and other herbaceous plants. Plant Molecular Biology Reporter, 13(3), 207-209.
Harbaugh, (1995) Flowering of Eustoma grandiflorum (Rat) Shinn. cultivars influenced by photoperiod and temperature. HortScience, 30(7), 1375-1377.
Hemming et al., (2008) Low-temperature and daylength cues are integrated to regulate Flowering Locus T in barley. Plant Physiology, 147(1), 355-366.
Hisamitsu et al.,(1998) Identification of endogenous gibberellins and their role in rosetted seedlings of Eustoma grandiflorum. Journal of the Japanese Society for Horticultural Science, 67(6), 866-871.
Kim et al., (2007) Delayed flowering time in *Arabidopsis* and *Brassica rapa* by the overexpression of Flowering Locus C (FLC) homologs isolated from Chinese cabbage (*Brassica rapaL*. ssp. pekinensis). Plant cell reports, 26(3), 327-336.
Landers et al., (1994) Genetic dissection of complex traits. Science, 265, 2037-2048.
Lee et al., (2007) Role of SVP in the control of flowering time by ambient temperature in *Arabidopsis*. Genes & development, 21(4), 397-402.
Michaels et al., (1999) Flowering Locus C encodes a novel MADS domain protein that acts as a repressor of flowering. The Plant Cell, 11(5), 949-956.
Nakano et al., (2011) Characterization of FLC, SOC1 and FT homologs in Eustoma grandiflorum: effects of vernalization and post-vernalization conditions on flowering and gene expression. Physiologia plantarum, 141(4), 383-393.
Ohkawa et al., (1997) Eustoma (Lisianthus)—its past, present, and future. In International Symposium on Cut Flowers in the Tropics 482, 423-428.
Ohkawa et al., (1991) Effects of air temperature and time on rosette formation in seedlings of Eustoma grandiflorum (Raf.) Shinn. Scientia horticulturae, 48(1-2), 171-176.

(Continued)

*Primary Examiner* — David H Kruse
(74) *Attorney, Agent, or Firm* — J. A. Lindeman & Co. PLLC

(57) ABSTRACT

Provided relates to a crop Lisianthus (*Eustoma grandiflorum*) plants that do not require cold treatment (vernalization) for the inductions of bolting and flowering, and to means and methods for producing same.

Figure 1:
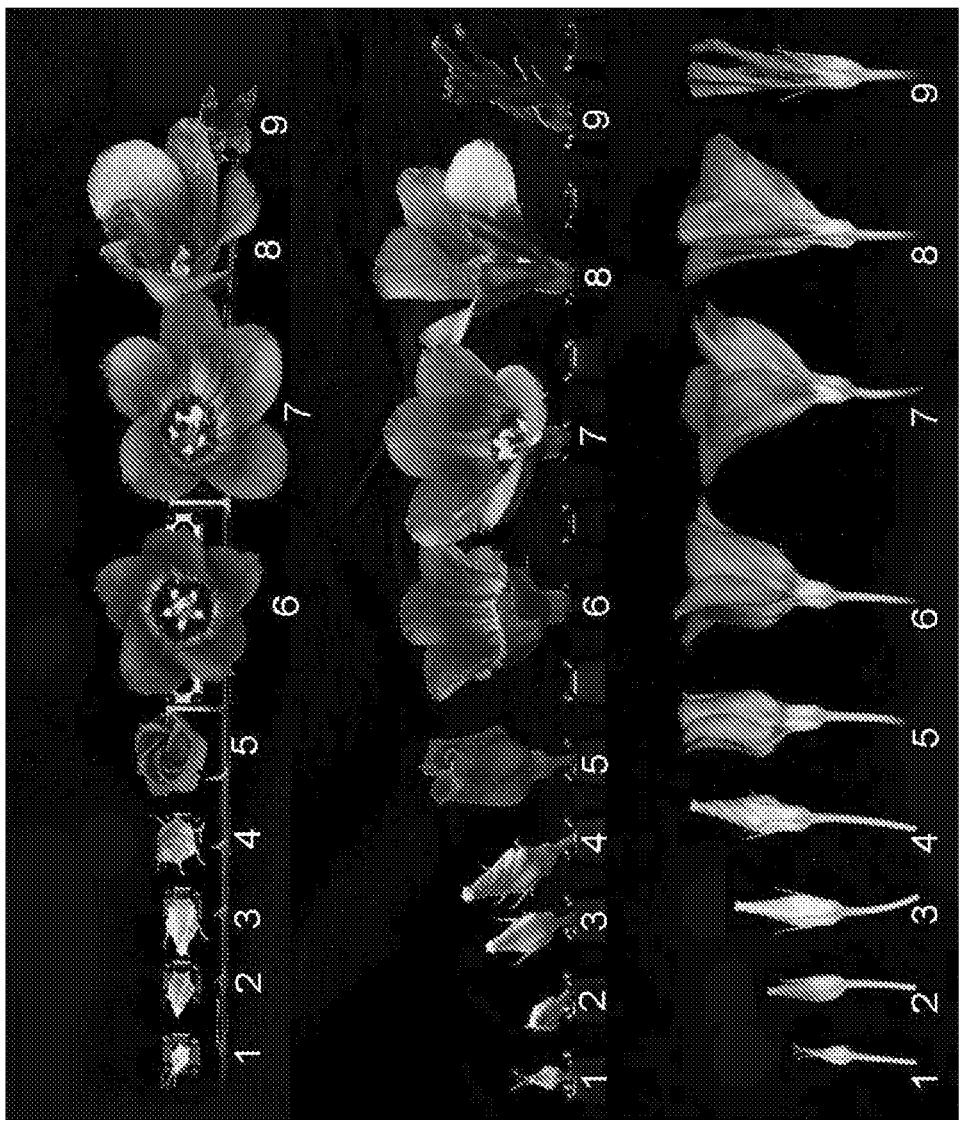

10 Claims, 18 Drawing Sheets
Specification includes a Sequence Listing.

(56) References Cited

OTHER PUBLICATIONS

Oka et al., (2001) Elevated sensitivity to gibberellin by vernalization in the vegetative rosette plants of Eustoma grandiflorum and *Arabidopsis thaliana*. Plant Science, 160(6), 1237-1245.

Potrykus, (1991) Gene transfer to plants: assessment of published approaches and results. Annual review of plant biology, 42(1), 205-225.

Ratcliffe et al., (2003) Analysis of the *Arabidopsis* MADS Affecting Flowering gene family: MAF2 prevents vernalization by short periods of cold. The Plant Cell, 15(5), 1159-1169.

Salehi et al., (2005) Delay in flowering and increase in biomass of transgenic tobacco expressing the *Arabidopsis* floral repressor gene Flowering Locus C. Journal of Plant Physiology, 162(6), 711-717.

Samach, (2013) Congratulations, you have been carefully chosen to represent an important developmental regulator!. Annals of botany, 111(3), 329-333.

Schranz et al., (2002) Characterization and effects of the replicated flowering time gene FLC in *Brassica rapa*. Genetics, 162(3), 1457-1468.

Shimamoto et al., (1989) Fertile transgenic rice plants regenerated from transformed protoplasts. Nature, 338(6212) 274-276.

Sung et al., (2005) Remembering winter: toward a molecular understanding of vernalization. Annu. Rev. Plant Biol., 56, 491-508.

Yamamoto et al., (2010) Ectopic expression of DnaK chaperone from a halotolerant cyanobacterium Aphanothece halophytica induced the bolting without cold treatment in Eustoma grandiflorum. Plant biotechnology, 27(5), 489-493.

Yanagida et al., (2004) Reduced glutathione is a novel regulator of vernalization-induced bolting in the rosette plant Eustoma grandiflorum. Plant and cell physiology, 45(2), 129-137.

Zamir, (2013) Where have all the crop phenotypes gone?. PLoS Biol, 11(6), e1001595.

Fujiwara and Kodama (2008) Characteristics of Wild Species of Eustoma and Breeding of Cultivars. Bulletin of Oita Prefectural Agriculture, Forestry and Fisheries Research Center, Agriculture Section No. 2, pp. 65-84. English summary on p. 84.

European Nucleotide Archive (ENA); Sequence: JK716389.1. EG0075c01 *Eustoma exaltatum* subsp. russellianum 3rd stage petal cDNA library *Eustoma exaltatum* subsp. russellianum cDNA, mRNA sequence. Published on Jan. 2, 2012. Retrieved from: https://www.ebi.ac.uk/ena/data/view/JK716389. 2 pages.

European Nucleotide Archive (ENA); Sequence: JK716390.1. EG0075c02 *Eustoma exaltatum* subsp. russellianum 3rd stage petal cDNA library *Eustoma exaltatum* subsp. russellianum cDNA, mRNA sequence. Published on Jan. 2, 2012. Retrieved from: ebi.ac.uk/ena/data/view/JK716390. 2 pages.

National Center for Biotechnology Information Search Database (NCBI); GenBank: AB565506.1. *Eustoma exaltatum* subsp. russellianum EgFLC gene for flowering locus C-like protein, splicing variant 1, flowering locus C-like protein, splicing variant 2, complete cds. Published on Apr. 6, 2011. Retrieved from: ncbi.nlm.nih.gov/nucleotide/AB565506.1?report=genbank&log$=nuclalig&blast_rank=1&RID=59E5Z9GG014. 2 pages.

* cited by examiner

SEQUENCE LISTING

<160> NUMBER OF SEQ ID NOS: 42

<210> SEQ ID NO 1
<211> LENGTH: 64
<212> TYPE: DNA
<213> ORGANISM: Eustoma exaltatum

<400> SEQUENCE: 1
cagctcttat gtgacataag aaatgttaca aaatgcatgc agtattcgat gtaaattacc      60
gacg                                                                  64

<210> SEQ ID NO 2
<211> LENGTH: 64
<212> TYPE: DNA
<213> ORGANISM: Eustoma exaltatum

<400> SEQUENCE: 2
ctgcaaacat cagtcttatt gcagttaaaa cagaaaatag gcatagaaaa acaagtaggg      60
aatg                                                                  64

<210> SEQ ID NO 3
<211> LENGTH: 590
<212> TYPE: DNA
<213> ORGANISM: Eustoma exaltatum

<400> SEQUENCE: 3
gaaggcaaaa attttttgagg agatgagccg caaaagagag agagcttctc aagccggcta     60
ctttccgagc tcttttccga aacgccggcg gcccagtgtc ccccgacgcg atctccccga    120
cgactcaaaa tttactctcg acgtcccctc ttccccggcg gcctcctcca agcagcaaaa    180
cacggtggtg gtgagtgggc tgccgaccga ttgctccgtg ttggacctga atcccgctt     240 cgagatctat ggctctatttt ctcgcacccg aatggaccct aatggtcttg cttacatcac    300
ttttcggtcc catgattccg ccacttccgc cgtctccgcc gccctcgacc cttctttccg    360
catcacctta ctctctaaac ctgtacaagt gatgtgggct actgacccgg taccgcagtg    420
gagggaaggt gtgacaaaga aagaaggtgc atcatcaaga ctgttgtctt caagctagtg    480
aggcctgacg tacctctatg tacgcgaggg agaggtaata aattgatttc agctattgtt    540
aatccagaga aaaggataat ggtaatggca ttggcaatga tgaaagggaa               590

<210> SEQ ID NO 4
<211> LENGTH: 64
<212> TYPE: DNA
<213> ORGANISM: Eustoma exaltatum

<400> SEQUENCE: 4
ctgcgattcc aaaaacgtgg aaggaagcaa actccgatgc aacaagttat tccctattga     60
atga                                                                  64

<210> SEQ ID NO 5
<211> LENGTH: 64
<212> TYPE: DNA
<213> ORGANISM: Eustoma exaltatum

<400> SEQUENCE: 5
cagcaccaaa taattcaatt gcctgatttt cccggtggaa tcgaggcttt tgagctatgt     60
gcta                                                                  64

```
<210> SEQ ID NO 6
<211> LENGTH: 64
<212> TYPE: DNA
<213> ORGANISM: Eustoma exaltatum

<400> SEQUENCE: 6
cagcaatgtt attcactggt ctctatctag tggcgctagg agttggaggc atcaagggat      60
ccct                                                                  64

<210> SEQ ID NO 7
<211> LENGTH: 64
<212> TYPE: DNA
<213> ORGANISM: Eustoma exaltatum

<400> SEQUENCE: 7
cagcatctgc gcacctgtta gtgcctgggg cgccacaaag tgaatgtatg ttaaagttaa      60
ggtt                                                                  64

<210> SEQ ID NO 8
<211> LENGTH: 64
<212> TYPE: DNA
<213> ORGANISM: Eustoma exaltatum

<400> SEQUENCE: 8
cagcaaaagt gcaatgatta gcaaccaagg cgccaaacag agcaacagtc caaattctaa      60
tagc                                                                  64

<210> SEQ ID NO 9
<211> LENGTH: 64
<212> TYPE: DNA
<213> ORGANISM: Eustoma exaltatum

<400> SEQUENCE: 9
ctgcattctg ttcaaaaagc atggccatgt taaacgtatc cagcaaaatt ttctccaaaa      60
gaaa                                                                  64

<210> SEQ ID NO 10
<211> LENGTH: 64
<212> TYPE: DNA
<213> ORGANISM: Eustoma exaltatum

<400> SEQUENCE: 10
ctgcattctt cattttggt actactccta tcttatagtc ttttgcatat tcctctgtgt       60
tttc                                                                  64

<210> SEQ ID NO 11
<211> LENGTH: 64
<212> TYPE: DNA
<213> ORGANISM: Eustoma exaltatum

<400> SEQUENCE: 11
cagcacctgg atttgggctt gaaaggggaa aagctgaggg tacacatact ggatttacag      60
ttgg                                                                  64

<210> SEQ ID NO 12
<211> LENGTH: 64
<212> TYPE: DNA
<213> ORGANISM: Eustoma exaltatum

<400> SEQUENCE: 12
```

```
ctgcttgaaa atttgttgca ggttcaaatg cgtgattcta tccgtggtca gccttgcctc      60
gatg                                                                   64

<210> SEQ ID NO 13
<211> LENGTH: 64
<212> TYPE: DNA
<213> ORGANISM: Eustoma exaltatum

<400> SEQUENCE: 13
cagctgtcca agttttgcac gcgccaaaag ctcgaccaga tcattctgag gcaattgtgg      60
agga                                                                   64

<210> SEQ ID NO 14
<211> LENGTH: 1400
<212> TYPE: DNA
<213> ORGANISM: Eustoma exaltatum

<400> SEQUENCE: 14
aagtaggtcg gagggggagt gcccttcctt ttgtgctcac tgctacgtaa cttcttcttt      60 ttgttttttgc gtggagtctt gacatcattg taacctattc tgatgctagg gtggtcatct    120
ttttgtatcg gccaaatccc tgggaatctg tgttcaccac ccccgtattt gatgagcaag    180
ctcttgccca aggttacac tttctttgat gcattatccc ctggactaca tcggctaacc     240
tattctgatt ctagggtggt cttcttttttg tatcggccaa atccctggga acctgtgttt    300 accaccccg gatttgatga gcaagctctt gctcaaagta actttctttg atgcattatc     360
ccctggacta cataggctag attatcttta actttgagac attttgtttc ctacactgac    420
aagtagatca ccattcattt ggcaatgaac ttatctcctt ggttgagcct atatcaagtc    480 tccgttttttc ctgcatgaat acaactttat ccttaattct tgccctgatc tttagacatt    540
gccattgaaa ctatttagtc cgggttctgc tttcgtcgag tcaacttctg tgtgaaagac    600
ggactagact catcatggaa gaaaacctta gagtcagatc actatgggca ccctcgagct    660
tatttgtttg ctttgagagg aattccataa ctagtccagc gcccaagaag ttgtttcagt    720
ccttggatat tttctcttgt gataacacag ttgtatctca ccataagcac tccatgaacc    780
cctttcaacg tttctccaaa ccaatatcag gacattgctg tgtataccga agccaattta    840
tacatttata gtgatttatc agggcacgaa attgacatta ctggatgata tttgtactac    900
atggtaatgc agaaatgcaa tccgattcat taacgcttta gcaagacacc acggaaagag    960
tatgcctttc tggccatgtt cttgcagcgt tctgaaatgc tccaacgaaa gctctttgcc   1020
aaaagaacgt taaaaaggc aggggatatg aacaatttca cagcacctag ctagtcgtac    1080
gttaactcgc accataaaaa tatgtaacag aaagagtaca ctccctccgt cccatcttat    1140
aattccacaa actattttga gatgtccaaa cttacaagtc tgcatgcttt aaattgtgaa    1200
agaaagcgga atcttttgct actttctcct tttctaaagt acacgcagtt aaaaaatgca    1260
cctaacttct tgtggcgaaa gttggaatac cttatttttat gctatgtctc acttccacaa    1320
ggtcttacat tttagaacag agggcagctg ctaatgatag tgccacttttc aaggaacaag    1380 gaaacaagac ccacctgatt                                                1400

<210> SEQ ID NO 15
<211> LENGTH: 64
<212> TYPE: DNA
<213> ORGANISM: Eustoma exaltatum

<400> SEQUENCE: 15
```

```
cagctctttc atcactgtga ggctcatagt ctggctgttc tgcatctgaa tttgaaacac    60
gtgc                                                                 64
```

<210> SEQ ID NO 16
<211> LENGTH: 64
<212> TYPE: DNA
<213> ORGANISM: Eustoma exaltatum

<400> SEQUENCE: 16

```
cagcaaaagt gaaatataag gtcttgcagt catgccgcct atgaccatct gaaaggatga    60
tttc                                                                 64
```

<210> SEQ ID NO 17
<211> LENGTH: 64
<212> TYPE: DNA
<213> ORGANISM: Eustoma exaltatum

<400> SEQUENCE: 17

```
ctgcaaaatt caaatgtgac gttttggtaa atcctcaacc ataacggagc ccaaacctct    60
gtga                                                                 64
```

<210> SEQ ID NO 18
<211> LENGTH: 64
<212> TYPE: DNA
<213> ORGANISM: Eustoma exaltatum

<400> SEQUENCE: 18

```
ctgcaccacc atgggataga ccaccagcat ttgaaccata aggttccata ttgaaagact    60
ggtt                                                                 64
```

<210> SEQ ID NO 19
<211> LENGTH: 64
<212> TYPE: DNA
<213> ORGANISM: Eustoma exaltatum

<400> SEQUENCE: 19

```
cagcaagtgg ctccatattg cttttatttg caaatatgca aatggttctc ctagataacc    60
gtgc                                                                 64
```

<210> SEQ ID NO 20
<211> LENGTH: 64
<212> TYPE: PRT
<213> ORGANISM: Eustoma exaltatum

<400> SEQUENCE: 20

Cys Ala Gly Cys Thr Gly Ala Ala Thr Gly Ala Gly Gly Cys Ala Cys
1               5                   10                  15

Thr Gly Ala Ala Cys Cys Thr Gly Ala Thr Cys Thr Thr Thr Gly Cys
            20                  25                  30

Ala Ala Thr Gly Cys Cys Ala Thr Thr Thr Gly Ala Gly Cys Cys Thr
        35                  40                  45

Gly Ala Cys Ala Cys Ala Ala Thr Gly Ala Gly Cys Thr Gly Gly Ala
    50                  55                  60

<210> SEQ ID NO 21
<211> LENGTH: 64
<212> TYPE: DNA
<213> ORGANISM: Eustoma exaltatum

<400> SEQUENCE: 21
ctgccgcctc ctgaatgaat gtgcgcggaa tgcagattga attcgtgctg aaaaaaaaaa     60
aaaa     64

<210> SEQ ID NO 22
<211> LENGTH: 64
<212> TYPE: DNA
<213> ORGANISM: Eustoma exaltatum

<400> SEQUENCE: 22
ctgcgatttc ttttcagatc tctagcatgg aaaagtgatt acctttatca gctagcctag     60
ttgc     64

<210> SEQ ID NO 23
<211> LENGTH: 64
<212> TYPE: DNA
<213> ORGANISM: Eustoma exaltatum

<400> SEQUENCE: 23
cagcatgcaa ctaggctagc tgataaaggt catcactttt ccatgctaga gatctgaaaa     60
gaaa     64

<210> SEQ ID NO 24
<211> LENGTH: 64
<212> TYPE: DNA
<213> ORGANISM: Eustoma exaltatum

<400> SEQUENCE: 24
ctgctaataa atttcttccc ccaaccccaa accccataa attactatct tgctgacgtg     60
gaaa     64

<210> SEQ ID NO 25
<211> LENGTH: 64
<212> TYPE: DNA
<213> ORGANISM: Eustoma exaltatum

<400> SEQUENCE: 25
cagctggaaa aagctttaga gaagacatat atgaatcctt gtttggagaa tatgaagggt     60
ggat     64

<210> SEQ ID NO 26
<211> LENGTH: 64
<212> TYPE: DNA
<213> ORGANISM: Eustoma exaltatum

<400> SEQUENCE: 26
ctgcctgaaa atttggagaa agagaagtcc tgaatcagtg tcctttacaa aatttaattg     60
gcat     64

<210> SEQ ID NO 27
<211> LENGTH: 566
<212> TYPE: DNA
<213> ORGANISM: Eustoma exaltatum

<400> SEQUENCE: 27
gaacaggatg tttgggataa ggatttggat atgtacaata attttttcca caaattgaaa     60
gtgattaagc agaacagtat tccaaaactc ttcctgttgg ccaattatat aaagtctaat    120
agagcaagtg tgtcagctgg tggtcttctct actcctggca ttgtcacgaa gccactacgc    180

```
gcaagtatgc tttctgcatc tctacgacgt gctatgggca gaggcacagg gtgtaatgga    240
gatgttcgta atctgactct ttctagtctg ctccatggga gaaaaattct agtagttgat    300
gataacaagg tcaatcttaa agtcgctgag ggtttcctca agaagtatgg ggctgaggtg    360
gtgcgagtgg aaagtggaaa agaagcagt ttcactgctg cagccacccc accaatttga    420
tgcctgtttc atggatattc aaatgccaga atggatggg tttgaagcaa caagagaat     480 tcggaacaca gaatatgaga tcaattctca gcttgaaagc ggagaacttt cagttgaaga    540
atatgcaaat ctttcaagtg gcatgt                                        566
```

<210> SEQ ID NO 28
<211> LENGTH: 64
<212> TYPE: DNA
<213> ORGANISM: Eustoma exaltatum

<400> SEQUENCE: 28

```
ctgcatttgg atcataaaca agagtgctgt agtaaggatc ctcctcctgt gaaacagca     60 gaaa                                                                 64
```

<210> SEQ ID NO 29
<211> LENGTH: 64
<212> TYPE: DNA
<213> ORGANISM: Eustoma exaltatum

<400> SEQUENCE: 29

```
cagcacaacg gatgccagtt acaatgtgca agagttgttt tggagcttca ccaatacaga    60
tatc                                                                 64
```

<210> SEQ ID NO 30
<211> LENGTH: 64
<212> TYPE: DNA
<213> ORGANISM: Eustoma exaltatum

<400> SEQUENCE: 30

```
ctgcctgagg tgtttcctgc ttttacatct tcagatggca tacaacatat gaactttgga    60
gtgg                                                                 64
```

<210> SEQ ID NO 31
<211> LENGTH: 64
<212> TYPE: PRT
<213> ORGANISM: Eustoma exaltatum

<400> SEQUENCE: 31

Cys Thr Gly Cys Thr Gly Thr Thr Thr Cys Ala Cys Ala Gly Gly
1               5                   10                  15

Ala Gly Gly Ala Gly Gly Ala Thr Cys Cys Thr Ala Thr Thr Ala
                20                  25                  30

Cys Ala Gly Cys Ala Cys Thr Cys Thr Gly Thr Thr Thr Ala Thr
            35                  40                  45

Gly Ala Thr Cys Cys Ala Ala Ala Thr Gly Cys Ala Gly Ala Ala
        50                  55                  60

<210> SEQ ID NO 32
<211> LENGTH: 64
<212> TYPE: DNA
<213> ORGANISM: Eustoma exaltatum

<400> SEQUENCE: 32

```
ctgccgctat tttctcgcgg agattgaact tctcagaaat tagcggccgg acatcttcag    60
cgcc                                                                 64

<210> SEQ ID NO 33
<211> LENGTH: 64
<212> TYPE: DNA
<213> ORGANISM: Eustoma exaltatum

<400> SEQUENCE: 33
cagcaaattg ttgacggatc tttggcctca atgattgacc cgtggttggc agaaaaaaaa    60
aaaa                                                                 64

<210> SEQ ID NO 34
<211> LENGTH: 64
<212> TYPE: DNA
<213> ORGANISM: Eustoma exaltatum

<400> SEQUENCE: 34
ctgcgctaga gcatgctaaa gcactagctg atcaggaatt gcagagaact acggaagaac    60
ttca                                                                 64

<210> SEQ ID NO 35
<211> LENGTH: 64
<212> TYPE: DNA
<213> ORGANISM: Eustoma exaltatum

<400> SEQUENCE: 35
ctgcttctca ttttgttgat ttggttaagt gctggctgga gaatgttgaa cagaacccaa    60
gcaa                                                                 64

<210> SEQ ID NO 36
<211> LENGTH: 64
<212> TYPE: DNA
<213> ORGANISM: Eustoma exaltatum

<400> SEQUENCE: 36
cagcttgaga tgtgcatatt gatcacagat ctcatgagat tttttcaccc tactatcacg    60
tgtc                                                                 64

<210> SEQ ID NO 37
<211> LENGTH: 64
<212> TYPE: DNA
<213> ORGANISM: Eustoma exaltatum

<400> SEQUENCE: 37
ctgcaaaatt tgattgagtc tttggatggc attgaacatc aaggtcattt ggcattcgag    60
acac                                                                 64

<210> SEQ ID NO 38
<211> LENGTH: 64
<212> TYPE: DNA
<213> ORGANISM: Eustoma exaltatum

<400> SEQUENCE: 38
ctgcacctca atacagagcc cgggaacatt aaacgttttg aacataatct caccagtgta    60
ttcc                                                                 64

<210> SEQ ID NO 39
<211> LENGTH: 64
```

```
<212> TYPE: DNA
<213> ORGANISM: Eustoma exaltatum

<400> SEQUENCE: 39
ctgcatatca tggtaatctt gattttgtag gtagagttct gaaagaaggg tatgatgtga    60
atct                                                                 64

<210> SEQ ID NO 40
<211> LENGTH: 64
<212> TYPE: DNA
<213> ORGANISM: Eustoma exaltatum

<400> SEQUENCE: 40
cagcaggagc ttgcaagcga agctccagga taagcacggt tcgtggctaa ccacctccgc    60
agaa                                                                 64

<210> SEQ ID NO 41
<211> LENGTH: 64
<212> TYPE: DNA
<213> ORGANISM: Eustoma exaltatum

<400> SEQUENCE: 41
ctgcagttat ttaatcaaac tgcctcttta aaaccttgat tcttgactca atgtgagggc    60
tagc                                                                 64

<210> SEQ ID NO 42
<211> LENGTH: 64
<212> TYPE: DNA
<213> ORGANISM: Eustoma exaltatum

<400> SEQUENCE: 42
ctgcaaatga aaccacaagt taacaaattg ccagattaaa atgatataac tgcaaatgaa    60
acca                                                                 64
```

VERNALIZATION INDEPENDENT LISIANTHUS PLANTS

SEQUENCE LISTING

The Sequence Listing submitted in text format (.txt) filed on May 24, 2017, named "SequenceListing.txt", created on May 24, 2017, 13.4 KB), is incorporated herein by reference."

FIELD OF THE INVENTION

The present invention relates to crop lisianthus (*Eustoma grandiflorum*) plants that do not require cold treatment (vernalization) for the inductions of bolting and flowering, and to means and methods for producing same.

BACKGROUND OF THE INVENTION

Lisianthus, *Eustoma grandiflorum* of the Gentianaceae family, is a relatively new floral crop to the international market, which is widely used as cut flower and also as potted plant. Common names for the naturally occurring plant are Texas Blue Bell, Prairie Rose and Prairie Gentian. Lisianthus is a diploid organism with ability for self and cross-pollination and almost all the seed in the commercial market are $F_1$ hybrids. The species *E. grandiflorum* originates from the prairies of the plain states in Northern America and is described as an annual or biennial that flowers in spring or early summer. The only other known species in the genus *Eustoma* is *E. exaltatum*, which is capable of cross pollination with *E. grandiflorum*. In a period of less than 30 years starting in the late $20^{th}$ century lisianthus shifted from being practically anonymous plant to being one of the top 10 cut flower crops in the world.

Attempts to transform the wild type bedding phenotype into the modern cut flower crop are going back to as early as 1930s and were mainly taken in Japan. However, a significant breakthrough occurred only in 1977 with the development of the first $F_1$ hybrids that were introduced to the international market around 1984 as a series of varieties by the name "Yodel". Breeding programs aiming at improved varieties for pot or bedding plants or for the cut flower market have started at late 1980s. Today, the lisianthus market is mainly focused on cut flower varieties.

The introduction of lisianthus as a crop plant has been slow, encountering cultivation and economical challenges including inadequate growth pattern, low flower yield, lack of uniformity and long growth period. The rising interest in this crop has lead to a parallel increase in scientific literature; however, it is still considered a floriculture example of an "orphan crop", a crop that is economically and culturally important but lacking a substantial research interest.

A limited work has been dedicated to examine trait inheritance in lisianthus, none of which combined molecular information and inheritance mechanism. Ecker et al. (Ecker R et al., 1993. Genet. Anal. 256: 253-257; Ecker R et al 1994. Euphytica 78: 193-197) showed a clear heterotic effect on growth rate, leaf size, stem diameter and number of nodes. The experiments were conducted on different inbred, $F_1$, $F_2$ and $BC_1$ populations with a wide genetic background. A model for seed dormancy inheritance was proposed based on an analysis of $F_1$, $F_2$ and $BC_1$ populations originated from a cross between genotypes requiring and genotypes not-requiring cold temperature for flowering. The model includes six diallelic loci with cumulative effects, in which the presence of at least nine 'dormancy-conferring' alleles is necessary for inducing phenotypic seed dormancy (Ecker R et al 1994. Plant Breed. 113: 335-339).

Lisianthus is considered a facultative long-day plant and although the photoperiod effect is considered to be minor, experiments have shown that a short day can have a delaying effect on flowering and also have a negative secondary effect on bolting (Harbaugh B K., 1995. HortScience. 30: 1375-1377).

The main environmental factor influencing growth and flower induction in lisianthus is temperature (Ohkawa K and Sasaki E., 1999. Acta Hortic. 482: 423-426). When lisianthus seedlings are exposed to temperatures above 20° C. for more than 14 days in the first growing stages, rosette growth occurs and elongation of flowering stem is delayed. Plants with rosette leaves will not bolt and flower very late in a scattered manner which is incompatible with agricultural production. Exposure to low temperature below 15° C. for at least 4 weeks (a process called "vernalization") has been proven to eliminate the negative effect of the high temperature (Ohkawa K et al., 1991. Sci. Hortic. (Amsterdam). 48: 171-176). Gibberellic acids (GAs) were found to play an important role in the vernalization effect by regulating stem elongation in a number of plants including lisianthus (Hisamatsu T et al., 1998. J. Japanese Soc. Hortic. Sci. 67: 866-871). Low temperatures can initiate GA biosynthesis and elevate GA sensitivity in vegetative rosette in *Arabidopsis thaliana* and lisianthus (Oka M et al., 2001. Plant Sci. 160: 1237-1245). Reduced glutathione (GSH) also has been shown to have a role in the response to vernalization in lisianthus, presumably by affecting regulation of bolting upstream of GA (Yanagida M et al., 2004. Plant Cell Physiol. 45: 129-37).

Lisianthus homologous of a few well-known genes that may play a role in the vernalization requirements have been investigated (Nakano Y et al., 2011. Physiol. Plant. 141: 383-93). The genes were selected based on their function in *Arabidopsis* vernalization mechanism. FLOWERING LOCUS C (FLC) encodes a MADS-box transcription factor and is a key repressor of flowering that is repressed by vernalization. FLOWERING LOCUS T (FT) and OVEREXPRESSION OF CONSTANS 1 (SOC1) are floral promoters that are suppressed by FLC. Function of the homologous lisianthus genes was examined by overexpressing the *Eustoma* genes in transgenic *Arabidopsis* plants. Expression analysis in different tissues and times for vernalized and non-vernalized plants indicated that EgFLCL (*E. grandiflorum* FLC-like) is up-regulated by cold temperatures and therefore defers from *Arabidopsis* FLC that is abundantly expressed before cold treatment and is silenced by vernalization. EgSOC1L (*E. grandiflorum* SOC1-like) and EgFTL (*E. grandiflorum* FT-like) were induced by warm temperatures and long day conditions following vernalization in a similar pattern to that observed for Barley Hv-FT1 which is induced by warm and long day conditions following vernalization (Hemming et al., 2008). These findings suggest that flowering regulation by vernalization in Eustoma differs considerably from the paradigm developed for *Arabidopsis thaliana* (Nakano et al., 2011, ibid).

The requirement to expose young seedling of lisianthus to temperatures below 15° C. for at least 4 weeks is a burden imposed on growers in terms of time and money, particularly in worm weather countries like Israel that are otherwise highly suitable for the production of lisianthus cut flowers.

Thus, there is still an unmet need for and it would be highly advantageous to have lisianthus (*Eustoma grandiflorum*) plants that are insensitive to vernalization and do not

SUMMARY OF THE INVENTION

The present invention provides ornamental lisianthus (*Eustoma grandiflorum*) plants with modulated vernalization requirements. Particularly, the present invention provides lisianthus plants that are not depended on vernalization to bolt and flower, which are highly suitable for agricultural commercial use.

The present invention is based in part on the unexpected discovery that introgression of minimal segment of chromosome equivalent to linkage group (LG) 2 of a wild *Eustoma exaltatum* into the genome of the ornamental crop lisianthus *E. grandiflorun* modified the vernalization requirement of *E. grandiflorun* such that bolting and flowering occurs without exposure to cold temperatures known to be required for this crop plant. The wild *E. exaltatum* accession used is vernalization independent, bolting without receiving a cold treatment that is required for bolting in *E. grandiflorum* plant devoid of said QTL or part thereof.

The *E. exaltatum* LG-2 segment comprises a QTL associated with at least one marker located between about 25 to about 45 cM. The introgressed *E. grandiflorum* plants of the present invention otherwise resemble elite plants in their appearance and agronomic requirements. Furthermore, the introgression of the *E. exaltatum*-derived QTL into *E. grandiflorun* results in an increase in the number of floral stems in a second flowering flush typical to this species.

According to one aspect, the present invention provides an ornamental *Eustoma grandiflorum* crop plant comprising a genetic element comprising QTL derived from linkage group (LG) 2 of *Eustoma exaltatum* or a part thereof, wherein the QTL or part thereof confers vernalization independence to the *E. grandiflorum* plant.

According to certain embodiments, the *E. exaltatum* plant comprising the QTL or part thereof is vernalization independent. According to certain exemplary embodiments, the vernalization independent *E. exaltatum* is *E. exaltatum* line 14_30 P1RI, seeds of which were deposited in NCIMB Ltd. on Nov. 23, 2015 under deposit number NCIMB 42491.

According to some embodiments, the genetic element consists of the QTL or part thereof conferring the vernalization independence.

According to some embodiments, the QTL or part thereof conferring the vernalization independence is associated with at least one marker located on *E. exaltatum* linkage group 2 in an interval stretched between 25-45 cM. According to some embodiments, the marker is any one of the markers listed in Table 1. Each possibility represents a separate embodiment of the present invention.

According to certain exemplary embodiments, the QTL or part thereof is associated with at least one marker located on *E. exaltatum* linkage group 2 in an interval stretched between 30-40 cM. According to some embodiment, the at least one marker comprises the nucleic acid sequence set forth in any one of SEQ ID NOs.:1-42. Each possibility represents a separate embodiment of the present invention.

According to some embodiment, the at least one marker comprises the nucleic acid sequence set forth in SEQ ID NO:3. According to other embodiment, the at least one marker comprises the nucleic acid sequence set forth in SEQ ID NO:15. According to additional embodiment, the at least one marker comprises the nucleic acid sequence set forth in SEQ ID NO:40.

According to certain exemplary embodiments, the QTL or part thereof is associated with the marker S1_74154018. According to certain exemplary embodiments, the marker is located at position 34.53167046 on *E. exaltatum* linkage group 2. According to some embodiments, the marker comprises the nucleic acid sequence CAGCTCTTTCATCACTGTGAGGCTCATAGTCTGGCTGTTCTGCATCTGAATTT GAAACACGTGC set forth in SEQ ID NO:15.

According to additional embodiments, the genetic element comprising the QTL or part thereof conferring the vernalization independence is incorporated within chromosome equivalent to linkage group 2 of the ornamental *E. grandiflorum*. According to certain exemplary embodiments, the genetic element comprising the QTL or part thereof is incorporated at a position from about 25 cM to about 45 cM on *E. grandiflorum* chromosome equivalent to linkage group 2.

According to some embodiments, the QTL or part thereof further confers an increase in the number of flower stems during a second flowering flush compared to the stem number during the second flush in a corresponding ornamental *E. grandiflorum* plant lacking the introduced QTL or parts thereof.

According to certain embodiments, the ornamental *E. grandiflorum* plant comprising the genetic element comprising the QTL or part thereof conferring the vernalization independence has equivalent agronomical traits compared to a corresponding ornamental *E. grandiflorum* plant lacking the introduced QTL or parts thereof. According to certain embodiments, the agronomical traits are selected from, but not limited to, pedicle length, growth rate, yield, resistance to abiotic stresses and resistance to pathogens. According to certain exemplary embodiments, the genetic element comprising the QTL or part thereof is introduced into an *E. grandiflorum* elite cultivar. It is to be understood that the *E. grandiflorum* of the present invention is an ornamental crop plat, but is not restricted to a specific line and/or variety.

According to certain exemplary embodiments, the flower pedicle length of *E. grandiflorum* comprising the QTL or part thereof is equivalent to the pedicle length of corresponding ornamental *E. grandiflorum* plant lacking the introduced QTL or parts thereof.

According to yet additional embodiments, the ornamental *E. grandiflorum* plant comprising the genetic element comprising the QTL or part thereof conferring the vernalization independence is devoid of deleterious genetic drags originated from the *E. exaltatum* chromosome.

According to certain embodiments, the plant is an inbred plant homozygous for the genetic element comprising the QTL or part thereof conferring the vernalization independence. According to other embodiments, the plant is a hybrid plant heterozygous for the genetic element comprising the QTL or part thereof conferring the vernalization independence. It is to be explicitly understood that plants heterozygous to the QTL or part thereof can bolt without receiving a cold treatment as described herein.

Seeds, cuttings and any other plant parts that can be used for propagation, including isolated cells and tissue cultures are also encompassed within the scope of the present invention. It is to be understood that the plant produced from said seeds or other propagating material comprises the QTL or part thereof conferring the vernalization independence.

The present invention discloses hitherto unknown association between QTL located on linkage group 2 of *E. exaltatum* and a constitutively vernalized phenotype, which, when transformed into the genome of *E. grandiflorum* results in its ability to bolt and flower without being exposed to vernalization cold temperatures known to be required for corresponding ornamental *E. grandiflorum* plant lacking the introduced QTL or parts thereof.

Thus, according to another aspect, the present invention provides an isolated polynucleotide comprising a nucleic acid sequence conferring vernalization independence, wherein the nucleic acid sequence is derived from a segment of chromosome equivalent to linkage group 2 of *E. exaltatum* plant, the *E. exaltatum* plant does not require vernalization to bolt and flower.

According to certain embodiments, the segment of *E. exaltatum* comprises a nucleic acid sequence located between 25 cM and 45 cM or part thereof. According to certain embodiments, the segment of *E. exaltatum* comprises the nucleic acid sequence of any one of the genetic markers listed in Table 1. According to other embodiments, the segment of *E. exaltatum* comprises a nucleic acid sequence located between 30 cM and 40 cM or part thereof. According to these embodiments, the segment comprises a nucleic acid sequence set forth in any one of SEQ ID NOs:1-42 or any combination thereof.

According to certain exemplary embodiments, the nucleic acids sequence comprises the sequence of the genetic marker S1_74154018, comprising the nucleic acid sequence set forth in SEQ ID NO:15.

According to yet additional aspect, the present invention provides a method for producing an ornamental *E. grandiflorum* independent on vernalization requirement for bolting, the method comprises introducing into *E. grandiflorum* a genetic element comprising QTL derived from linkage group 2 of *Eustoma exaltatum* or a part thereof, wherein the QTL or part thereof confers vernalization independence to the *E. grandiflorum* plant, thereby producing ornamental *E. grandiflorum* independent on vernalization requirement for flowering.

According to certain embodiments, the *E. exaltatum* plant comprising the QTL or part thereof is vernalization independent.

According to certain exemplary embodiments, the vernalization independent *E. exaltatum* plant comprising the QTL or part thereof is *E. exaltatum* line 14_30 P1RI, seeds of which were deposited in NCIMB Ltd. on Nov. 23, 2015 under deposit No. NCIMB 42491.

According to some embodiments, the genetic element consists of the QTL or part thereof conferring the vernalization independence.

According to some embodiments, the QTL or part thereof conferring the vernalization independence is associated with at least one marker located on *E. exaltatum* linkage group 2 at from about 25 to about 45 cM or any combination thereof. According to some embodiments, the at least one genetic marker is selected from the group listed in Table 1. Each possibility represents a separate embodiment of the present invention. According to other embodiments, the QTL or part thereof is associated with at least one marker located on *E. exaltatum* linkage group 2 at from about 30 to about 40 cM or any combination thereof. According to these embodiments, the at least one genetic marker comprises the nucleic acid sequence set forth in any one of SEQ ID NOs:1-42.

According to certain exemplary embodiments, the QTL or part thereof is associated with the marker S1_74154018, comprising the nucleic acid sequence set forth in SEQ ID NO:15.

According to certain embodiment, the genetic element comprising the QTL or part thereof is introduced into chromosome equivalent to linkage group 2 of *E. grandiflorum*. According to certain exemplary embodiments, the segment is introduced at a location of from about 25 cM to about 45 cM of *E. grandiflorum* linkage group 2.

Any method as is known to a person skilled in the art can be used to introduce the genetic element comprising the QTL or part thereof into *E. grandiflorum*.

According to certain exemplary embodiments, the genetic element is introduced by introgression.

According to other embodiments, the genetic element is introduced by transformation.

According to certain embodiments, selecting *E. grandiflorum* plants that bolt independently on a vernalization treatment is performed by detecting the presence of the QTL or part thereof derived from *E. exaltatum* described herein within the genome of the *E. grandiflorum* plant. Any method as is known in the art can be used to detect the QTL or part thereof. According to certain exemplary embodiments, detection is performed by identifying the markers located within the QTL as described herein.

Other objects, features and advantages of the present invention will become clear from the following description and drawings.

BRIEF DESCRIPTION OF THE FIGURES

FIG. 1 demonstrates the nine different development stages defined from early bud stages (stage 1) to senescence (stage 9). The picture shows flowers of $F_1$ hybrid obtained from a cross between *E. grandiflorum* Pink parent and *E. exaltatum*.

FIG. 2 shows plants that did not bolt and are at the rosette state (FIG. 2A) and bolted plants (FIG. 2B).

FIG. 3 shows different flower phenotypes. FIG. 3A: Variation in stamen number. FIG. 3B: Variation on stigma lobes. FIG. 3C: Pedicel length. FIG. 3D: Sepal length.

FIG. 4 provides schematic presentation of the construction of two recombinant inbred (RI) mapping populations.

FIG. 5 shows estimated marker linkage of the combined recombinant inbred lisianthus population. The line indicates linkage (large LOD score or small recombination fraction) and the background indicates unlinked markers (small LOD score or large recombination fraction).

FIG. 6 shows the lisianthus linkage map composed of 4500 SNPs markers and 69 linkage groups.

FIG. 7 shows Manhattan Plot: The lisianthus Rosetting QTL on the combined homozygous RI linkage map constructed using the genotype-by-sequencing (GBS) data.

FIG. 8 shows a detailed view of the lisianthus Rosetting QTL on linkage group 2 of the combined homozygous RI linkage map constructed using the GBS data.

FIG. 9 presents a comparison of the mean number of bolting plants homozygous for the *E. grandiflorum* allele of S1_74154018 (1) and plants homozygous for the *E. exaltatum* S1_74154018 allele (3).

FIG. 10 shows Manhattan Plot: The lisianthus Rosetting QTL on the combined heterozygous RI linkage map constructed using the genotype-by-sequencing (GBS) data.

FIG. 11 shows a detailed view of the lisianthus Rosetting QTL on linkage group 2 of the combined heterozygous RI linkage map constructed using the GBS data.

FIG. 12 presents a comparison of the mean number of bolting plants homozygous for the *E. grandiflorum* allele of S1_74154018 (1) and the heterozygous plants comprising one *E. grandiflorum* allele and one *E. exaltatum* allele of S1_74154018 (2).

FIG. 13 shows bolting of hybrid heterozygous plant comprising the vernalization independence allele (designated F1p) and of vernalization-dependent commercial varieties. FIG. 13A: percentage of bolting. FIG. 13B: picture of a flowering F1p plant. FIG. 13C: picture of Rosita 3 Green plant with rosette leaf phenotype.

Figure 14:
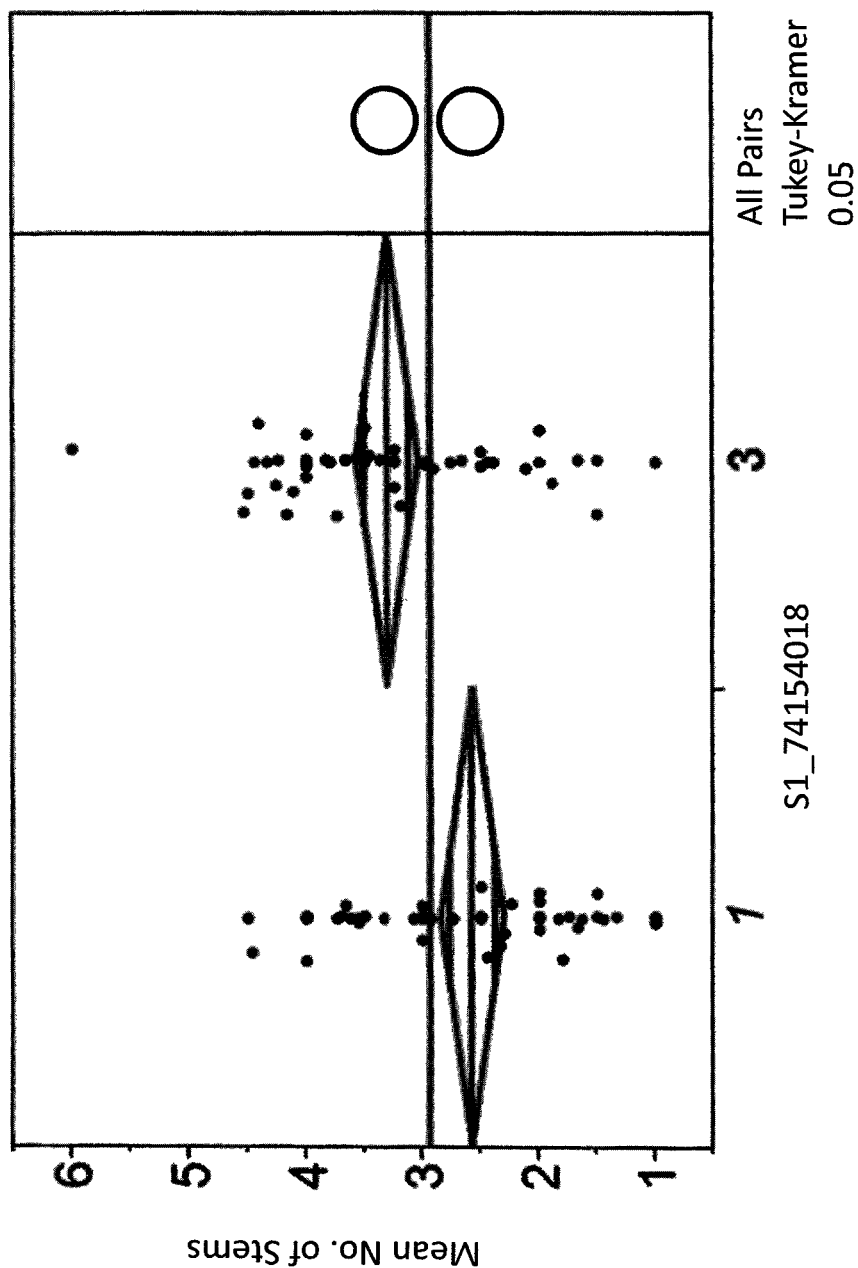

FIG. 14 presents a comparison of the mean number of stem per plants in the second flowering flush between plants homozygous for the *E. grandiflorum* allele of S1_74154018 (1) and the plants homozygous for the *E. exaltatum* allele (3).

Figure 15:
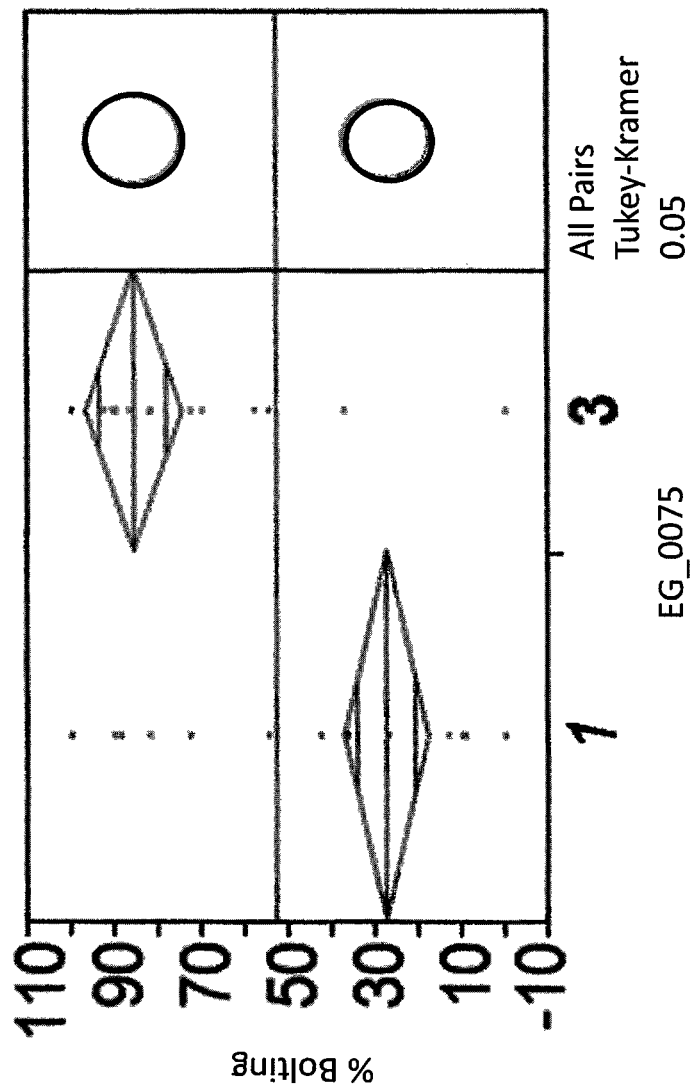

FIG. 15 presents a comparison of the mean number of bolting plants homozygous for the *E. grandiflorum* allele of EG_0075 (1) and plants homozygous for the *E. exaltatum* EG_0075 allele (3).

Figure 16:
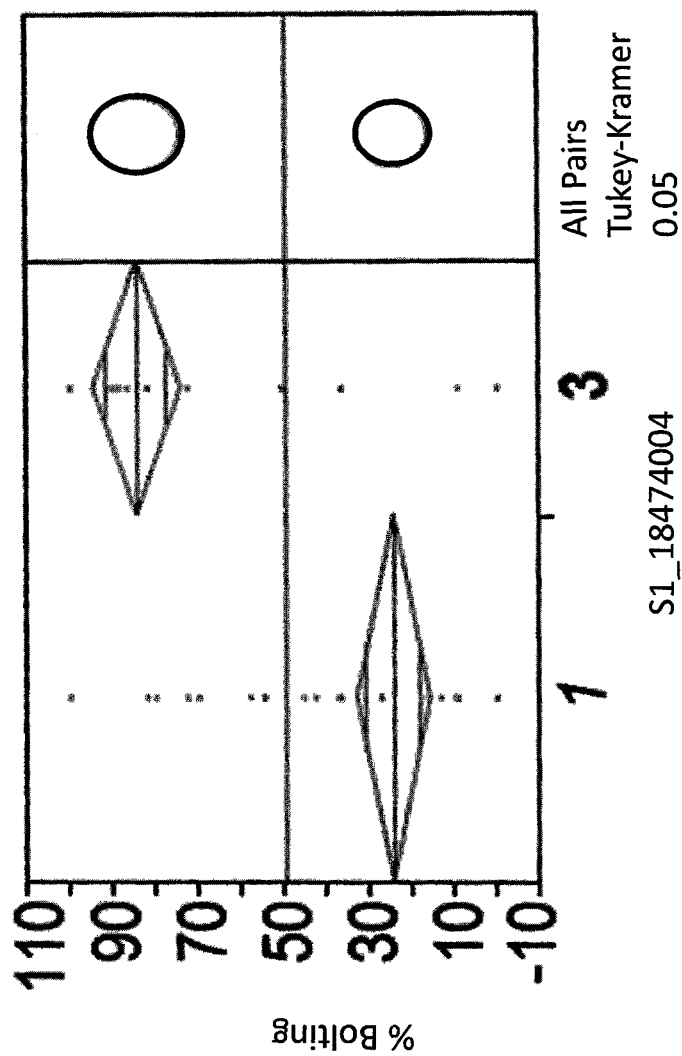

FIG. 16 presents a comparison of the mean number of bolting plants homozygous for the *E. grandiflorum* allele of S1_18474044 (1) and plants homozygous for the *E. exaltatum* S1_18474044 allele (3).

DETAILED DESCRIPTION OF THE INVENTION

Definitions

The term "plant" is used herein in its broadest sense. It also refers to a plurality of plant cells that are largely differentiated into a structure that is present at any stage of a plant's development. Such structures include, but are not limited to, a root, stem, shoot, leaf, flower, petal, fruit, etc. According to certain exemplary embodiments, the terms "ornamental plant" or "ornamental crop plant" used interchangeably herein, particularly in reference to *Eustoma grandiflorum* refer to lines suitable for commercial growth for their cut flowers and as a garden or pot plants.

As used herein, the term "plant part" typically refers to a part of the lisianthus plant, including single cells and cell tissues such as plant cells that are intact in plants, cell clumps and tissue cultures from which lisianthus plants can be regenerated. Examples of plant parts include, but are not limited to, single cells and tissues from pollen, ovules, leaves, embryos, roots, root tips, anthers, flowers, fruits, stems, shoots, and seeds; as well as pollen, ovules, leaves, embryos, roots, root tips, anthers, flowers, fruits, stems, shoots, scions, rootstocks, seeds, protoplasts, calli, and the like.

As used herein, the term "bolting" refers to the transition from the vegetative or rosette stage to the inflorescence or reproductive growth stage.

The term "vernalization" as used herein refers to the process by which floral induction in some plants is promoted by exposing the plants to chilling for certain duration. According to certain embodiments, the term "vernalization" in reference to lisianthus (*Eustoma*) includes exposure of seedlings in the first growing stage to low temperature of below 20° C., sometimes below 18° C. or below 15° C. The term "first growing season" refers to a time period from appearance of the first leaves and during about at least three weeks or about four weeks or more. As used herein, the terms "vernalization independence" or vernalization independent" refer to lisianthus plants grown under optimal conditions known in the art for the commercial growth that bolt and flower essentially without the vernalization treatment.

The term "locus" (plural "loci") is defined herein as the position that a given gene occupies on a chromosome of a given species.

As used herein, the term "linkage group" refers to all of the genes or genetic traits that are located on the same chromosome. Within the linkage group, those loci that are close enough together will exhibit linkage in genetic crosses. Since the probability of crossover increases with the physical distance between genes on a chromosome, genes whose locations are far removed from each other within a linkage group may not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous to (the physical entity of) chromosome.

The term "QTL" is used herein in its art-recognized meaning. The term "QTL conferring vernalization independence" refers to a region located on a particular chromosome of *Eustoma* that is associated with at least one gene that encodes for vernalization independence or at least a regulatory region, i.e. a region of a chromosome that controls the expression of one or more genes involved in vernalization independence. The phenotypic expression of that gene may be, for instance, bolting without the need for cold treatment and/or increase in the number of flowers in a second flowering flush. A QTL may for instance comprise one or more genes of which the products confer the vernalization independence. Alternatively, a QTL may for instance comprise regulatory genes or sequences of which the products influence the expression of genes on other loci in the genome of the plant thereby conferring the vernalization independence. The QTL of the present invention may be defined by indicating its genetic location in the genome of the respective *E. exaltatum* accession using one or more molecular genomic markers. One or more markers, in turn, indicate a specific locus. Distances between loci are usually measured by frequency of crossing-over between loci on the same chromosome and expressed as centimorgan (cM). The further apart two loci are, the more likely that a crossover will occur between them. Conversely, if two loci are close together, a crossover is less likely to occur between them. As a rule, one centimorgan (Kosambi map function (cM)) is approximately equal to 1% recombination between loci (markers). When a QTL can be indicated by multiple markers the genetic distance between the end-point markers is indicative of the size of the QTL.

The term "natural genetic background" is used herein to indicate the original genetic background of a QTL. Such a background is the genome of *Eustoma exaltatum*, particularly *E. exaltatum* that does not require vernalization to flower. Accordingly, *E. exaltatum* line 14_30 P1RI represents the natural genetic background of the QTL of the invention. A method that involves the transfer of DNA comprising the QTL or a part thereof, from linkage group 2 of *E. exaltatum* to the same or different position on the corresponding chromosome of another *Eustoma* species will result in that QTL or part thereof not being in its natural genetic background.

The term "heterozygous" as is used herein means a genetic condition existing when different alleles reside at corresponding loci on homologous chromosomes.

The term "homozygous" as is used herein, means a genetic condition existing when identical alleles reside at corresponding loci on homologous chromosomes.

As used herein, the term "hybrid" refers to any offspring of a cross between two genetically unlike individuals, including but not limited to the cross between two inbred lines.

As used herein, the term "inbred" means a substantially homozygous individual plant or plant line.

The terms "introgression" "introgressed" and "introgressing" refer to the transmission of a desired allele(s) of a gene or trait locus from a genetic background of one species, variety or cultivar into the genome of another species, variety or cultivar. In one method, the desired allele(s) can be introgressed through a sexual cross between two parents, wherein one of the parents has the desired allele in its genome. The desired allele can include desired gene or genes, a marker locus, a QTL or the like.

As used herein, the term "population" refers to a genetically heterogeneous collection of plants sharing a common genetic derivation.

The terms "genetic engineering", "transformation" and "genetic modification" are all used herein for the transfer of isolated and cloned genes into the DNA, usually the chromosomal DNA or genome, of another organism, or to the modification of a gene within the plant genome.

The terms "molecular marker" or "DNA marker" are used herein interchangeably and refer to a molecular indicator that is used in methods for visualizing differences in characteristics of nucleic acid sequences. Examples of such indicators are diversity array technology (DArT) markers, restriction fragment length polymorphism (RFLP) markers, amplified fragment length polymorphism (AFLP) markers, single nucleotide polymorphisms (SNPs), insertion mutations, microsatellite markers, sequence-characterized amplified regions (SCARs), cleaved amplified polymorphic sequence (CAPS) markers or isozyme markers or combinations of the markers described herein which defines a specific genetic and chromosomal location. The DNA markers used in the present invention are mostly Genotype By Sequencing (GBS markers).

According to one aspect, the present invention provides an ornamental crop *Eustoma grandiflorum* plant comprising a genetic element comprising QTL derived from linkage group 2 of *Eustoma exaltatum* or a part thereof, wherein the QTL or part thereof confers vernalization independence to the *E. grandiflorum* plant.

The present invention discloses for the first time a quantitative trait locus (QTL) associated with vernalization independence in lisianthus, hitherto known to have obligatory requirement for low temperature at the early growth stages in order to produce commercially adequate crops of cut flowers. The QTL was observed in the non-commercial species of lisianthus, *Eustoma exaltatum*. Upon analyses of a vast number of phenotypes and their related genotypes the QTL that essentially abolishes the requirement to vernalization was found to be located on linkage group 2 of *E. exaltatum* plant having a vernalization independence phenotype. The plant used in the course of the present invention was *E. exaltatum* line 14_30 P1RI. Seeds of this line have been deposited with NCIMB Ltd., Ferguson Building, Craibstone Estate, Bucksburn, Aberdeen, AB21 9YA, Scotland, an International Depository Authority under the Budapest Treaty. The date of deposit was Nov. 23, 2015. The deposit of seeds is a representative sample of material that was in existence prior to the filing date of this application. The NCIMB I.D. number is NCIMB 42491.

According to certain embodiments, the QTL or part thereof conferring the vernalization independence is associated with at least one marker located on *E. exaltatum* linkage group 2 in an interval stretched between 25-45 cM. According to certain embodiments, the at least one marker is selected from the markers presented in Table 1 below. Each possibility represents a separate embodiment of the present invention.

TABLE 1

Markers associated with the QTL conferring vernalization independence (25-45 cM)

| Marker Identification (Name) | Linkage group | Location | Potential Gene |
|---|---|---|---|
| S1_79899029 | 2 | 25.2729168 | |
| S1_132303063 | 2 | 25.3591237 | |
| S1_32459047 | 2 | 25.3591237 | |
| S1_91483027 | 2 | 25.4655066 | |
| S1_82327059 | 2 | 25.8313603 | |
| S1_19123049 | 2 | 27.1012016 | |
| S1_147358035 | 2 | 27.2231528 | |
| S1_87807054 | 2 | 27.5035266 | |
| S1_93482040 | 2 | 27.7947888 | |
| S1_1787059 | 2 | 28.3452475 | Alligator *sinensis* DNA-damage regulated autophagy modulator 1 (DRAM1), mRNA |
| S1_96902033 | 2 | 28.5413259 | |
| S1_148336028 | 2 | 28.671196 | |
| S1_33221020 | 2 | 28.671196 | |
| S1_22227029 | 2 | 28.8862498 | |
| EG0387 | 2 | 29.3716867 | *Solanum tuberosum* nitrate transporter 1.7-like (LOC102595468), mRNA |
| S1_73884050 | 2 | 29.9902434 | |
| S1_87283016 | 2 | 30.2963658 | |
| EG0075 | 2 | 30.5046992 | *Nicotiana tomentosiformis* uncharacterized LOC104104277 (LOC104104277), mRNA |
| S1_123945039 | 2 | 30.7345842 | |
| S1_11829060 | 2 | 30.8495268 | *Gossypium raimondii* BTB/POZ domain-containing protein At1g67900-like (LOC105785819), transcript variant X2, mRNA |
| S1_9324035 | 2 | 30.8495268 | |
| S1_25202031 | 2 | 32.0033729 | |
| S1_821031 | 2 | 32.4795634 | |
| S1_106431037 | 2 | 32.8465359 | |
| S1_106444061 | 2 | 33.9132025 | |
| S1_13214061 | 2 | 34.1696128 | |
| S1_146447048 | 2 | 34.1696128 | |
| S1_77887034 | 2 | 34.1696128 | |
| M364 | 2 | 34.3481842 | *Eustoma exaltatum* subsp. *russellianum* EgFLC gene for flowering locus C-like protein |
| S1_74154018 | 2 | 34.5316705 | *Eustoma exaltatum* subsp. *russellianum* EgFLC gene for flowering locus C-like protein |
| S1_818061 | 2 | 34.6234136 | |
| S1_87134020 | 2 | 34.6234136 | |
| S1_94713045 | 2 | 34.6234136 | |
| S1_7596056 | 2 | 34.8936839 | |
| S1_74857018 | 2 | 34.9814032 | |
| S1_116205031 | 2 | 35.0698987 | |
| S1_124042040 | 2 | 35.0698987 | |
| S1_25957031 | 2 | 35.2468899 | |
| S1_132575046 | 2 | 35.4320751 | |
| S1_76085030 | 2 | 35.7291048 | |
| S1_119861024 | 2 | 36.1638874 | |
| EG0251 | 2 | 36.4455775 | *Solanum lycopersicum* histidine kinase 3 (LOC101247719), mRNA |
| S1_107206032 | 2 | 36.6378852 | |
| S1_10323014 | 2 | 36.9440077 | |

TABLE 1-continued

Markers associated with the QTL conferring vernalization independence (25-45 cM)

| Marker Identification (Name) | Linkage group | Location | Potential Gene |
|---|---|---|---|
| S1_120016062 | 2 | 36.9440077 | |
| S1_144019030 | 2 | 37.2700946 | |
| S1_116491060 | 2 | 37.3700946 | |
| S1_3153042 | 2 | 37.6379518 | |
| S1_126482027 | 2 | 377272375 | |
| S1_145987039 | 2 | 37.7272375 | *Sporobolomyces roseus* clone JGIBAIF-21A8 |
| S1_82366053 | 2 | 37.7272375 | |
| S1_87161029 | 2 | 37.7272375 | |
| S1_95462030 | 2 | 37.8149568 | *Drosophila grimshawi* GH15291 (Dgri\GH15291), mRNA |
| S1_102889027 | 2 | 38.0091315 | |
| S1_18474044 | 2 | 38.2014392 | |
| S1_101739044 | 2 | 39.3221289 | |
| S1_88239020 | 2 | 39.8028981 | |
| S1_97044021 | 2 | 40.5381922 | |
| S1_105014027 | 2 | 40.8013501 | |
| S1_130428020 | 2 | 40.8013501 | |
| S1_142182032 | 2 | 40.8013501 | |
| S1_27670063 | 2 | 40.921832 | |
| S1_103249035 | 2 | 41.0437833 | |
| S1_85145041 | 2 | 41.4478237 | |
| S1_138550028 | 2 | 41.7603237 | |
| S1_15369024 | 2 | 42.8129552 | |
| S1_115528043 | 2 | 43.4512531 | |
| S1_3171045 | 2 | 44.2355668 | |
| S1_99369052 | 2 | 45.1284240 | |

According to certain exemplary embodiments, the QTL or part thereof conferring the vernalization independence is associated with at least one marker located on E. exaltatum linkage group 2 in an interval stretched between 30-40 cM. According to certain embodiments, the at least one marker is selected from the markers listed in Table 2 below. According to these embodiments, the at least one marker comprises the nucleic acid sequence set forth in any one of SEQ ID NOs:1-42. Each possibility represents a separate embodiment of the present invention.

TABLE 2

Markers associated with the QTL conferring vernalization independence (30-40 cM)

| Marker Identification (Name) | Linkage group | Location | LOD | SEQ ID NO. |
|---|---|---|---|---|
| S1_73884050 | 2 | 29.9902434 | 4.74 | 1 |
| S1_87283016 | 2 | 30.2963658 | 7.10 | 2 |
| EG0075 | 2 | 30.5046992 | 10.28 | 3 |
| S1_123945039 | 2 | 30.7345842 | 6.65 | 4 |
| S1_11829060 | 2 | 30.8495268 | 7.28 | 5 |
| S1_9324035 | 2 | 30.8495268 | 5.79 | 6 |
| S1_25202031 | 2 | 32.0033729 | 7.63 | 7 |
| S1_821031 | 2 | 32.4795634 | 10.46 | 8 |
| S1_106431037 | 2 | 32.8465359 | 9.46 | 9 |
| S1_106444061 | 2 | 33.9132025 | 10.02 | 10 |
| S1_13214061 | 2 | 34.1696128 | 17.01 | 11 |
| S1_146447048 | 2 | 34.1696128 | 15.84 | 12 |
| S1_77887034 | 2 | 34.1696128 | 18.03 | 13 |
| M364 | 2 | 34.3481842 | 19.08 | 14 |
| S1_74154018 | 2 | 34.5316705 | 21.71 | 15 |
| S1_818061 | 2 | 34.6234136 | 16.68 | 16 |
| S1_87134020 | 2 | 34.6234136 | 18.44 | 17 |
| S1_94713045 | 2 | 34.6234136 | 19.17 | 18 |
| S1_7596056 | 2 | 34.8936839 | 13.29 | 19 |
| S1_74857018 | 2 | 34.9814032 | 11.05 | 20 |

TABLE 2-continued

Markers associated with the QTL conferring vernalization independence (30-40 cM)

| Marker Identification (Name) | Linkage group | Location | LOD | SEQ ID NO. |
|---|---|---|---|---|
| S1_116205031 | 2 | 35.0698987 | 12.59 | 21 |
| S1_124042040 | 2 | 35.0698987 | 10.68 | 22 |
| S1_25957031 | 2 | 35.2468899 | 13.36 | 23 |
| S1_132575046 | 2 | 35.4320751 | 10.92 | 24 |
| S1_76085030 | 2 | 35.7291048 | 11.14 | 25 |
| S1_119861024 | 2 | 36.1638874 | 5.91 | 26 |
| EG0251 | 2 | 36.4455775 | 16.82 | 27 |
| S1_107206032 | 2 | 36.6378852 | 12.06 | 28 |
| S1_10323014 | 2 | 36.9440077 | 12.73 | 29 |
| S1_120016062 | 2 | 36.9440077 | 14.36 | 30 |
| S1_144019030 | 2 | 37.2700946 | 13.04 | 31 |
| S1_116491060 | 2 | 37.3700946 | 14.83 | 32 |
| S1_3153042 | 2 | 37.6379518 | 13.09 | 33 |
| S1_126482027 | 2 | 377272375 | 11.53 | 34 |
| S1_145987039 | 2 | 37.7272375 | 12.73 | 35 |
| S1_82366053 | 2 | 37.7272375 | 14.49 | 36 |
| S1_87161029 | 2 | 37.7272375 | 13.49 | 37 |
| S1_95462030 | 2 | 37.8149568 | 13.78 | 38 |
| S1_102889027 | 2 | 38.0091315 | 9.59 | 39 |
| S1_18474044 | 2 | 38.2014392 | 12.80 | 40 |
| S1_101739044 | 2 | 39.3221289 | 5.88 | 41 |
| S1_88239020 | 2 | 39.8028981 | 4.00 | 42 |

The genetic unit "QTL" indicates a region on the genome that is directly related to a phenotypic quantifiable trait, the need of lisianthus plant for vernalization to bolt and flower according to the present invention. QTL differs from the genetic unit "gene", on which the phenotypic expression depends on a large number of factors that cannot be predicted. Several markers of the QTL identified in the present invention have been found to be located within known genes (see Table 1). These genes may or may not play a role in the QTL inheritable trait of vernalization independence, disclosed by the present invention for the first time.

A specific trait is associated with a particular marker or markers. The markers disclosed in the present invention indicate the location of the QTL and furthermore, correlate to the presence of the specific phenotypic trait of vernalization independence in a plant. It is to be noted that the contiguous genomic markers that indicate the location of the QTL on the genome are in principal arbitrary or non-limiting. In general, the location of a QTL is indicated by a contiguous string of markers that exhibit statistical correlation to the phenotypic trait. Once a marker is found outside that string (i.e. one that has a LOD-score below a certain threshold, indicating that the marker is so remote that recombination in the region between that marker and the QTL occurs so frequently that the presence of the marker does not correlate in a statistically significant manner to the presence of the phenotype) the boundaries of the QTL are set. Thus, it is also possible to indicate the location of the QTL by other markers located within that specified region. LOD scores of the exemplary markers of the present invention appear in Table 2 hereinabove.

According to additional embodiments of the invention, the contiguous genomic markers can also be used to indicate the presence of the QTL (and thus of the phenotype) in an individual plant, i.e. they can be used in marker assisted selection (MAS) procedures. In principle, the number of potentially useful markers is limited, but a large number of markers can be also used. The skilled person may easily identify additional markers to those disclosed in the present application. Any marker that is linked to the QTL, e.g.

falling within the physically boundaries of the genomic region spanned by the markers having established LOD scores above a certain threshold thereby indicating that no or very little recombination between the marker and the QTL occurs in crosses; as well as any marker in linkage disequilibrium to the QTL may be used in MAS procedures. Accordingly, the markers identified in the present invention as associated to the QTL, including the marker S1_74154018, are mere examples of markers suitable for use in MAS procedures. Moreover, when the QTL, or the specific trait-conferring part thereof, is introgressed into another genetic background (i.e. into the genome of another plant species), then some markers may no longer be found in the offspring although the trait is present therein, indicating that such markers are outside the genomic region that represents the specific trait-conferring part of the QTL in the original parent line only and that the new genetic background has a different genomic organization.

According to certain embodiments, the markers associated with the QTL of the present invention are listed in Table 1. According to other embodiments, the markers associated with the QTL of the present invention are listed in Table 2, having the nucleic acid sequence set forth in SEQ ID NOs:1-42. According to some exemplary embodiments, the QTL or part thereof is associated with a marker selected from the comprising group consisting of marker EG0075, having the nucleic acid sequence set forth in SEQ ID NO:3; marker S1_74154018 having the nucleic acid sequence set forth in SEQ ID NO:15 and marker S1_18474044 having the nucleic acid sequence set forth in SEQ ID NO:40. Each possibility represents a separate embodiment of the present invention.

According to certain exemplary embodiments, the QTL or part thereof is associated with the marker S1_74154018. According to certain embodiments, the marker comprises the nucleic acid sequence set forth in SEQ ID NO:15.

Introgression of the QTL into the genome of the crop species *E. grandiflorum* resulted in plants that bolt and develop flowering stems without being first exposed to low temperatures. Unexpectedly, the introgression had minor or null deleterious effect on the growth pattern and on the flowers produced. Furthermore, the introgression not only affected the vernalization requirement, but resulted in an increased number of flowering stems per plant in the second flowering flush typically induced in commercial growth of lisianthus. Together, these two traits, reducing the cost involved in the agricultural growth and elevating the yield provide for a significant commercial value.

Introducing the genetic element comprising the QTL or part thereof that abolishes the need for vernalization for lisianthus to bolt can be performed by any method as is known to a person skilled in the art. It is to be explicitly understood that in the *E. grandiflorum* produced, the segment comprising the QTL is not in its natural background.

A nucleic acid (preferably DNA) sequence comprising the QTL of the present invention or any part thereof that can reduce or eliminate the vernalization requirement as disclosed herein may be used for the production of the ornamental *E. grandiflorum*. According to certain embodiments, the QTL is introduced into *E. grandiflorum* that requires vernalization for adequate bolting and flowering, typically a variety suitable for commercial growth. According to the teachings of the present invention, said nucleic acid sequence is derived from *E. exaltatum* donor plant.

The QTL or part thereof conferring vernalization independence can be isolated from the donor plant by using any method as is known in the art.

The QTL sequence or a part thereof conferring vernalization independence may be transferred to a recipient lisianthus plant by any method as is known to a person skilled in the art. According to certain embodiments, the QTL or part thereof can be introduced by crossing the QTL donor with the recipient lisianthus, particularly *E. grandiflorum* (i.e. by introgression). Alternatively, isolated nucleic acid sequence comprising the QTL or part thereof can be introduced by transformation as described hereinbelow. Transformation is optionally followed by selection of offspring plants comprising the QTL and exhibiting independence of vernalization.

The QTL of the present invention may be isolated and its nucleic acid sequence may be determined by any method as is known to the skilled person. For example, a nucleic acid sequence comprising the QTL or a vernalization independence conferring part thereof may be isolated from *E. exaltatum* donor plant by fragmenting the genome of said plant and selecting those fragments harboring one or more markers indicative of said QTL disclosed herein. Subsequently or alternatively, the marker sequences (or parts thereof) indicative of said QTL may be used as amplification primers, using e.g. PCR, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

According to certain aspects of the invention there is provided an isolated polynucleotide comprising a nucleic acid sequence conferring vernalization independence, wherein the nucleic acid sequence is derived from a segment of chromosome equivalent to linkage group 2 of *E. exaltatum* plant, wherein the *E. exaltatum* plant does not require vernalization to bolt and flower.

Transforming plants with isolated nucleic acid sequence generally involves the construction of an expression vector that will function in plant cells. According to the teachings of the present invention, such a vector comprises the QTL of the invention or part thereof. Typically, the vector comprises the QTL or part thereof under control of or operatively linked to a regulatory element. According to certain embodiments, the regulatory element is selected from the group consisting of a promoter, and enhancer and a translation termination sequence. The vector(s) may be in the form of a plasmid, and can be used, alone or in combination with other plasmids, in a method for producing transgenic *E. grandiflorum* plants that do not require vernalization in order to bolt using transformation methods known in the art to be suitable for transforming nucleic acid sequences into lisianthus plants.

Expression vectors can include at least one marker (reporter) gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the markers gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, the presence of the QTL in the transformed plant is identified using the QTL-associated markers as probes.

Methods for transforming a plant cell with nucleic acids sequences according to the present invention are known in the art. As used herein the term "transformation" or "transforming" describes a process by which a foreign nucleic acid sequence, such as a vector, enters and changes a recipient cell into a transformed, genetically modified or transgenic cell. Transformation may be stable, wherein the nucleic acid sequence is integrated into the plant genome and as such represents a stable and inherited trait, or transient, wherein the nucleic acid sequence is expressed by the cell transformed but is not integrated into the genome, and as such represents a transient trait. According to typical embodiments the nucleic acid sequence of the present invention is stably transformed into a plant cell.

There are various methods of introducing foreign genes into both monocotyledonous and dicotyledonous plants (for example, Potrykus I. 1991. Annu Rev Plant Physiol Plant Mol Biol 42:205-225; Shimamoto K. et al., 1989. Nature 338:274-276).

The principal methods of the stable integration of exogenous DNA into plant genomic DNA includes two main approaches:

*Agrobacterium*-mediated gene transfer: The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the *Agrobacterium* delivery system in combination with vacuum infiltration.

Direct nucleic acid transfer: There are various methods of direct nucleic acid transfer into plant cells. In electroporation, protoplasts are briefly exposed to a strong electric field, opening up mini-pores to allow DNA to enter. In microinjection, the nucleic acid is mechanically injected directly into the cells using micropipettes. In microparticle bombardment, the nucleic acid is adsorbed on microprojectiles such as magnesium sulfate crystals or tungsten particles, and the microprojectiles are physically accelerated into cells or plant tissues. Another method for introducing nucleic acids to plants is via the sonication of target cells. Alternatively, liposome or spheroplast fusion has been used to introduce expression vectors into plants.

Following transformation of lisianthus target tissues, expression of the above described selectable marker genes allows for preferential selection of transformed cells, tissues and/or plants, using regeneration and selection methods now well known in the art.

Alternatively, the QTL or part thereof according to the teachings of the present invention may be transformed without prior isolation of the vernalization independence conferring nucleic acid sequence.

According to certain exemplary embodiments, the transfer of the QTL or part thereof is performed by introgression of *E. exaltatum* linkage group segment into an *E. grandiflorum* that requires vernalization for bolting and flowering.

According to certain embodiments, the method comprises the steps of:
 a. providing a parent *E. grandiflorum* plant line that requires cold treatment for bolting and flowering and an *E. exaltatum* plant that does not require cold treatment for bolting and flowering, the *E. exaltatum* plant comprising a QTL associated with the marker S1_74154018;
 b. crossing the parent *E. grandiflorum* plant line with the *E. exaltatum* plant to produce $F_1$ progeny plants;
 c. selfing the $F_1$ progeny plants to produce F2 population;
 d. backcrossing the F2 population with the parent *E. grandiflorum* line at least once to produce backcross population;
 e. selecting from the backcross population *E. grandiflorum* plants comprising the QTL associated with the marker S1_74154018.

According to certain embodiments, step (d) of backcrossing the $F_2$ population with the parent *E. grandiflorum* line is repeated 5 times to produce backcross population 5.

According to some embodiments, the *E. grandiflorum* plants comprising the QTL associated with the marker S1_74154018 does not require vernalization to bolt and flower.

Selecting *E. grandiflorum* plants comprising the QTL associated with the marker S1_74154018 can be performed by any method as is known in the art.

According to some embodiments, selection of QTL-comprising plant comprises detecting the presence of the marker associated with the QTL described herein.

The detection method may comprise the steps of providing an oligonucleotide or polynucleotide capable of hybridizing under stringent hybridization conditions to a nucleic acid sequence of a marker linked to said QTL, preferably selected from the markers identified herein as being linked to said QTL, contacting said oligonucleotide or polynucleotide with a genomic nucleic acid obtained from a plant of the backcross population, and determining the presence of specific hybridization of said oligonucleotide or polynucleotide to said genomic nucleic acid.

Alternatively, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in lisianthus plants suspected to be vernalization independent.

The phrase "stringent hybridization conditions" refers to conditions under which a probe or polynucleotide will hybridize to its target subsequence, typically in a complex mixture of nucleic acids, but to essentially no other sequences. Stringent conditions are sequence-dependent and will be different in different circumstances. Longer sequences hybridize specifically at higher temperatures. An extensive guide to the hybridization of nucleic acids is found in Tijssen (Tijssen P. 1993 Hybridization With Nucleic Acid Probes. Part I. Theory and Nucleic Acid Preparation. In: Laboratory Techniques in Biochemistry and Molecular Biology. Elsevier). Generally, stringent conditions are selected to be about 5-100 C lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 300 C for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. Additional guidelines for determining hybridization parameters are provided in numerous references, e.g. Current Protocols in Molecular Biology, eds. Ausubel, et al. 1995.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods
Plant Material

The lisianthus project at the Robert H. Smith Faculty of Agriculture, Food and Environment, The Hebrew University of Jerusalem, includes hundreds of different breeding lines and genetic resources that originated from over 50 commercial hybrids from six different breeding companies as well as wild *E. grandiflorum* and *E. exaltatum* that were obtained from a variety of sources.

Seedling Production and Plant Growing Conditions

Sowing was done, inter alia, in Hishtil Ltd. Israel, at the Nehalim nurseries (Israel) in 360 or 406 standard lisianthus sowing trays. Seedlings were grown at the facilities of Hishtil Ltd. Company, Israel. Up to year 2010, the seedlings were grown in Hishtil nursery at Nehalim and from 2011 in Susya (Israel). The seedlings were grown under standard commercial hybrids growing conditions and the standard lisianthus low temperature (vernalization) requirements were met.

Typically, selections and seed production were conducted in the farm of the Faculty of Agriculture, Food and Environment of the Hebrew University of Jerusalem, located in Rehovot, Israel. Flowering season always occurred in spring to summer (April to August) depending on the time of sowing. Irrigation and fertilization were given according the standard lisianthus protocols and in accordance with the growing conditions and growth stage. Crop protection treatments were given only after specific appearance of symptoms and only before the beginning of flowering. First flower was snapped off in plants used for phenotypic characterization. Harvesting was carried out at second flower anthesis.

Flower Pollination and Seed Handling
 Self-pollination:
  1. A flower between stage 3 (bud starts to swells, petals are higher than sepals) and stage 6 (stamens discharged, closed stigma, FIG. 1) was covered with a paper bag.
  2. 5-14 days after the flower has been covered, the bag was opened and manual self-pollination was done. After pollination the flower was reclosed within the paper bag.

Only seeds that were produced by manual self-pollination were considered to be a true self-pollination seeds.
 Cross-pollination:
  1. Stage 3 flowers (bud starts to swells, petals are higher than sepals, FIG. 1) were manually opened and the anthers were removed. Each of the castrated flowers was closed in a paper bag.
  2. 7-14 days after removal of the anthers the paper bag of each flower was opened and pollen was manually applied on stigma by either attaching an anther of the male parent to the stigma or by using a brush sterilized with 70% ethanol and covered with the pollen. After the manual pollination, the flower was reclosed in the paper bag.

After 50-75 days from pollination (both for self and cross-pollination), the fruit were harvested into paper bags and kept in an incubator or a dry oven at 37-45° C. to complete drying. The seeds were stored at ±7° C. and 30% humidity until sowing.

Phenotypic Characterization

The traits described herein are based on an extensive phenotypic effort to characterize a large number of traits, based on which 113 traits were selected to create a detailed phenotypic catalog for the characterization of the genetic populations.

In order to standardize the different phenotypic characteristics, it was necessary to define a common language of a few terms:

Floral stage: Nine different development stages were defined from early bud stages to senescence, as depicted in FIG. 1. Stage 1: Closed bud, sepals are higher (longer) than petals; Stage 2: Beginning of bud swelling, sepals and petals are roughly the same length; Stage 3: Large bud, sepals are shorter than petals, swollen bud; Stage 4: Petals beginning to unfold, stamens are not fully matured; Stage 5: Flower starts to open, petals are separated, stamens are not discharged, stigma is closed; Stage 6: Open flower, stamens discharged, closed stigma; Stage 7: Anthesis, stamens discharged, open stigma; Stage 8: Flower begins to wilt, petals fade and start to close; Stage 9: Senescence.

Branch: only branches with two or more pairs of leaves were defined as branches.

Flower bud: only flower buds that aroused from bracts and were more than one cm long were defined as flower buds.

Flowering time: the day in which the first flower reached developmental stage 6 (open flower, stamens discharged, closed stigma, FIG. 1).

Harvesting time: the day in which the second flower reached developmental stage 7 (anthesis, FIG. 1).

Figure 2A:
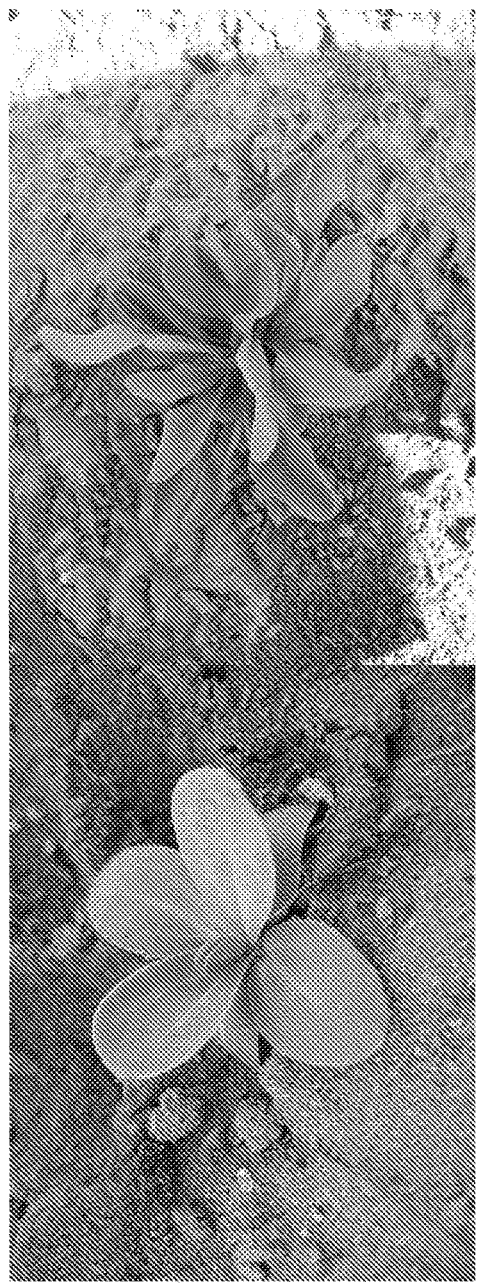
Figure 2B:
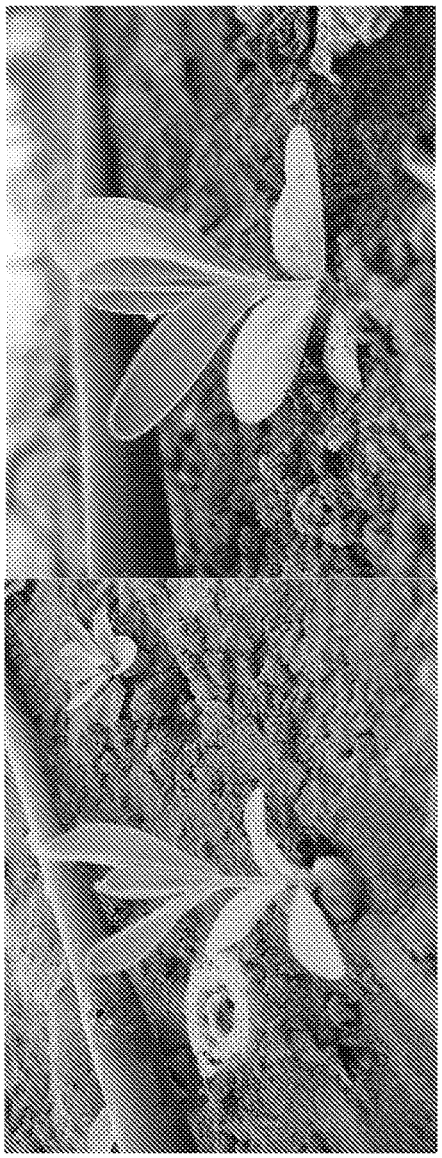

Bolting: transition of a plant from vegetative growth to flowering was identified by appearance and elongation of a stem (FIG. 2). Degree of bolting was defined by three different time points:
 (a) Bolting 18 week [bolting (18)]: Percentage of bolting plants per line 18 weeks after sowing.
 (b) Bolting 20 week [bolting (20)]: Percentage of bolting plants per line 20 weeks after sowing.
 (c) Bolting 22 week [bolting (22)]: Percentage of bolting plants per line 22 weeks after sowing.

Second-flush related traits: number of traits that describe the plant after harvest of flowers of the first flush and during growth up to the second flush of flowering.
 (a) Second flush survival [SF. survival]: Percentage of plants per line that survived after the harvest and had a second flush of flowers.

(b) Second flush stems per plant [SF.S_PLN]: Number of brunches per plant in the second flush.

(c) Rosetting in second flush [SF.rosettin]: Percentage of plants per line that showed rosette and did not bolt after first harvest (FIG. 2A).

(d) Days to second flush [SF.days]: Minimal number of days per line from first to second harvest (second flush harvest).

Flower organ size: the size of the different flower organs was measured with a roller (during year 2011) or by image analysis (during year 2012).

Figure 3A:
Figure 3B:
Figure 3D:
Figure 3C:
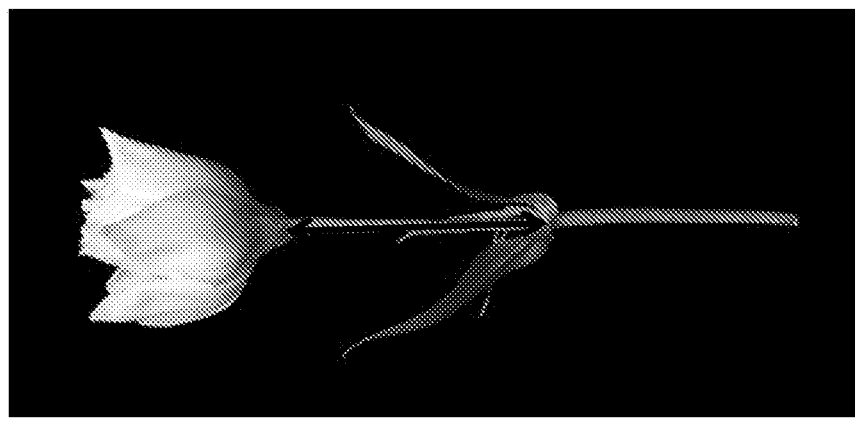

(a) Pedicel length [Pedicel.LN]: The length of the last internode bearing the flower on the main stem, measured by a roller in all seasons (FIG. 3C).

The phenotypic analyses were carried out through four main experiments:

Year 2011 Greenhouse—Plants were grown hydroponically in a plastic greenhouse with no heating in eight liter pail containers. Growing medium used was "Odem 93" (Tuff Marom Golan Ltd., Israel) (⅔ tuff, ⅓ peat). Every recombinant inbred line (RIL) was planted in three containers distributed randomly in the greenhouse. Each container contained five RIL replicates (total of 15 replicates per RIL). In addition, six replicates from each RIL ware planted in a single container for breeding and characterization on a family level. Total size of greenhouse was 150 m². Planting date was Feb. 15, 2011; flowering had begun on Apr. 22, 2011.

Year 2012 Greenhouse—Plants were grown in an identical manner and in the same greenhouse as described for the experiment of year 2011. As the experiment of this year included backcross lines (BCLs) F5BC1, due to space constrains each line was planted in two containers only (total of 10 replicates per line). Planting date was Jan. 12, 2012; flowering had begun on Apr. 15, 2011.

Year 2012 NetHouse—Plants were grown hydroponically in a net-house in big one-row plastic containers containing a two phase growing medium of thin tuff layer over of rough tuff layer. Six replicates from every line were planted in a single location. Plants were grown at a density of 30 plants per m². Total size of the net-house was 100 m². Planting date was Jan. 12, 2012; flowering had begun on May 22, 2012.

Year 2013 SHTIL NETO Greenhouse—Plants were grown in a plastic greenhouse in large seedling trays (1.5 inch) containing peat. 177 different lines (total of 11 replicates per line). Sowing date—Jul. 29, 2013; end of bolting—Oct. 20, 2013.

The phenotypic analyses were preformed along the entire growing season from germination to harvesting. The main analysis was focused around the flowering period and was conducted as follows: three times a week (Sunday, Tuesday and Thursday) apart from the specific events of holidays, etc., the first flower to open from each plant was recorded, photographed and removed. Plants that continue to grow and reached harvesting time (as defined hereinabove) were harvested. Phenotyping of the harvested plant was conducted at the day of harvest and at the following day. Other phenotyping analyses not performed in regard with the harvested plants as well as phenotyping the cut flower placed in a vase and breeding work was performed in alternative days to the harvesting days.

DNA Extraction

Fresh young leave were harvested and frozen immediately by liquid nitrogen. Frozen tissue was kept in −80° C. until DNA extraction. DNA extraction was carried out using standard microprep protocol (Fulton T M et al., 1995. Plant Mol. Biol. Report. 13: 207-209).

QTL Analysis

QTL mapping analyses were performed on the averaged row data for each population and experiment separately. Heterozygote genotypes for a specific marker in the RIL were removed from analysis of the marker. By averaging the traits score per line in an experiment both the ordinal and binary (yes/no phenotypes) traits were transformed to traits with a nominal nature. Shapiro-Wilk tests were conducted to examine the normality assumption of each trait distribution and the traits were categorized as those displaying normal versus non-normal phenotypic distributions. LOD scores were calculated by following the methods for normal and non-normal phenotype distributions (Borman K W and Sen S., 2009. A guide to QTL mapping with R/qtl 1st ed. (Springer New York)). In general, for the normally distributed traits, the $\log_{10}$ likelihood ratio test, which is similar to one-way ANOVA (marker regression), was applied, while the Kruskal-Wallis test statistic divided by 2(ln10) was used for the non-normal distributed traits. All calculations were done by R statistical software. QTL effect was calculated as a percentage of difference attributed to the homozygote wild type allele in the RIL or the heterozygote allele in the BCL.

$$\text{Effect }(RIL) = \frac{\mu(exs) - \mu(gra)}{\mu(exs)} \times 100$$

$$\text{Effect }(BCL) = \frac{\mu(het) - \mu(gra)}{\mu(het)} \times 100$$

wherein: $\mu(gra)$=trait average of the homozygote *E. grandiflorum* plants for the QTL; $\mu(exs)$=trait average of the homozygote *E. exaltatum* plants for the QTL; $\mu(het)$=trait average for the heterozygote plants for the QTL.

The assigning of the QTL's was done in a few stages: 1. Phenotype genotype connection above the threshold of 2.5 LOD score in at least one of the experiments in one of the populations was selected. 2. As the threshold can be lowered due to the prior discovery of the QTL (Lander E S and Schork N J., 1994. Science 265(5181): 2037-2048.), all experiments that showed above 1 LOD score (<0.031 p value) for the connections selected in stage 1 were declared as experiments that show the QTL. 3. If a number of neighboring markers were correlated to the same trait, the main QTL for the trait was chosen based on the number of experiments in which the linkage was observed and by the LOD scores. If the QTL was detected only in one net house experiment it was dropped as this experiments suffered from reduced biological repeats due to experimental design (only one plot per line) and/or a higher number of plants effected by scirtothrips infestation and therefore were less reliable.

For the QTL map a trait was selected to represent the QTL in the case where a few closely related traits are connected to the same Loci. The trait that was assigned was a trait that showed significance in more experiments or a trait with a higher average LOD score in the case of same number of significant experiments. The effect to be shown on the map was selected in the following order in the case of a few significant experiments: 1. White population, 2012; 2. White population, 2011; 3. Pink population, 2012; 4. Pink population, 2011.

Example 1

Recombinant Inbred Lines (RILs)

During the year 2006 more than 140 crosses were performed between different pure lines derived from commercial hybrids and from wild accessions of E. grandiflorum and E. exaltatum (collection of the Hebrew University of Jerusalem, Israel). Phenotypic characterization of the $F_1$ populations and their parents, in the year 2007, allowed the selection of two interspecific recombinant inbred lines (RIL) populations used in the study presented herein. The selection was based mainly on: (A) Homozygosity of the parental lines as observed from the phenotype; (B) Uniformity of the $F_1$; and (C) phenotypic characteristics of the parent lines. Ultimately two genetic introgression populations were selected for an in depth examination.

Figure 4:
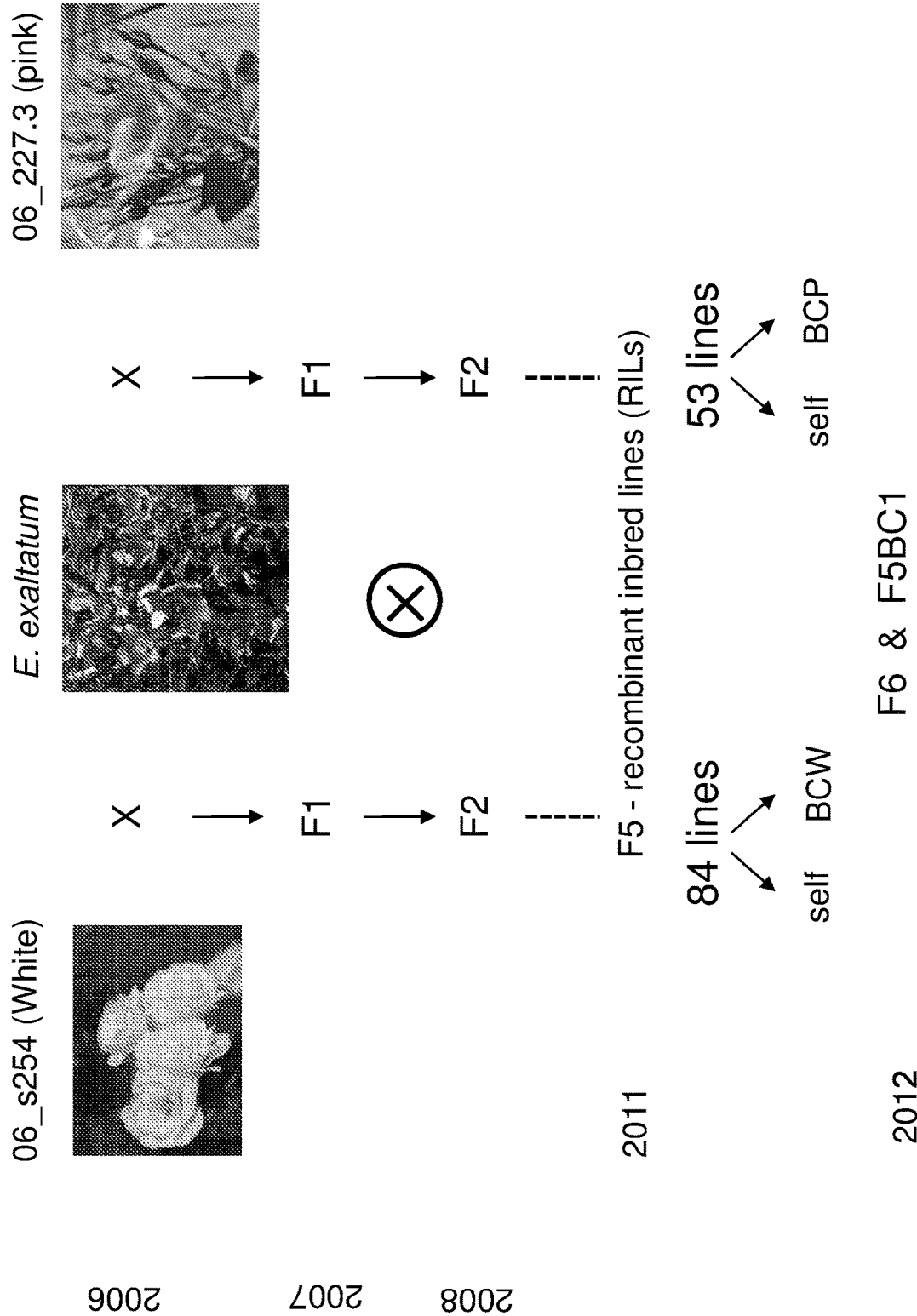

The two RIL populations were constructed from a cross between E. exaltatum and two E. grandiflorum lines from cultivated backgrounds of Pink and White flowers. The main characteristics of the parent lines are: E. exaltatum: small single purple flower, bushy growth, late flowering, strong circadian rhythm movement, narrow leaves and narrow stems with no tendency to form rosettes. The accession used for the crosses showed very high uniformity, which indicated it was a homozygous pure line. E. grandiflorum Pink: medium size single flower, intense pink color, weak apical dominance, short internodes, high flower yield, tendency to rosette and overall a typical summer variety growth (good heat tolerance, slow growing). E. grandiflorum White: big double white flower, many petals, strong apical dominance, low flower yield and overall a typical winter variety growth (moderate temperature requirements for bolting, fast growth). The $F_5$ RIL lines were backcrossed to their E. grandiflorum parents in order to create the backcross lines (BCL). A schematic description of the constructions of the two RIL is presented in FIG. 4.

Example 2

Phenotypic Data

Phenotypic observations were performed for two separate progenies in two locations. In 2011 the two RIL populations in one location were characterized; in 2012 two RIL and two BCL populations in two locations were characterized (Table 3). The experiments always included the parental lines and the $F_1$ progenies and the statistical analysis was based on multiple repeats that were planted in a random manner (see material and method hereinabove).

TABLE 3

Summary of the Phenotypic Collection

| Population type* | Year | Location | Number of traits | Number of trait groups** | Average replicas per genotype |
|---|---|---|---|---|---|
| RIL | 2011 | Greenhouse | 89 | 8 | 13.9 |
| RIL, BCL | 2012 | Greenhouse | 104 | 8 | 10.1 |
| RIL, BCL | 2012 | Net-house | 83 | 6 | 4.9 |
| | Total traits common to all experiments | | 81 | 6 | |

*All experiments included also the parental lines, original $F_1$ and a control hybrid variety.
**The different traits were assigned to phenotypic groups as described in the phenotypic catalog (see material and methods).

Example 3

Genetic Map

Two genetic maps were constructed with the available genetic markers for each of the RIL population.

Figure 5:
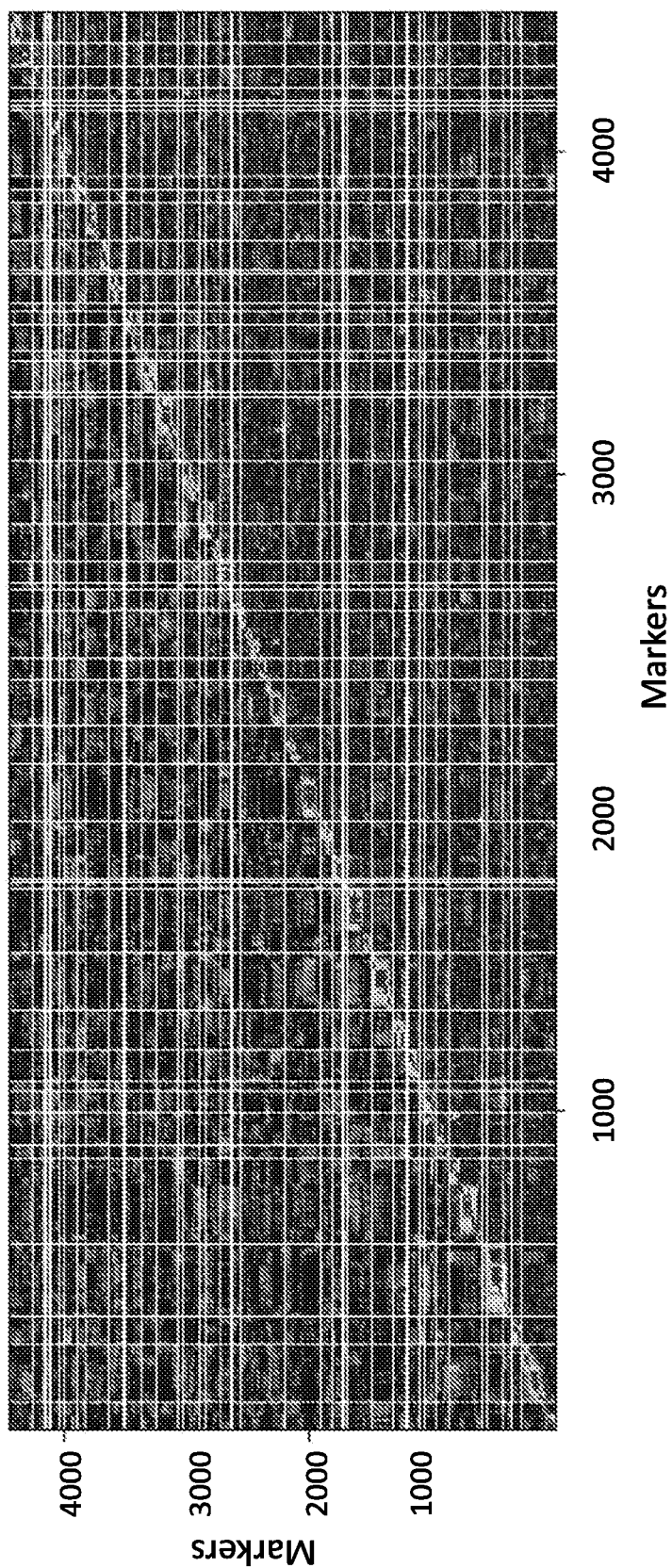
Figure 6:
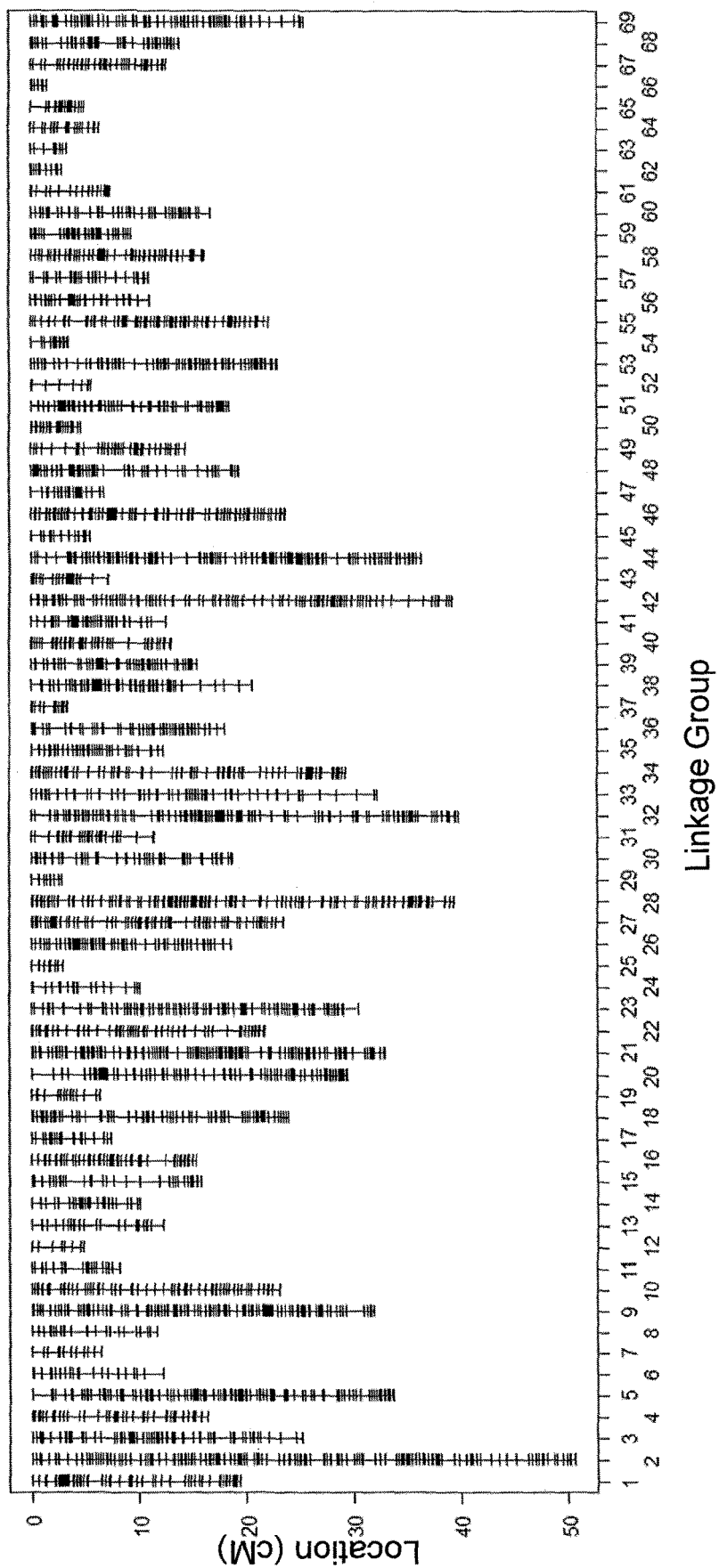

The DNA polymorphism data was generated using the genotype-by-sequencing (GBS) platform available as a service at Cornell University at the Institute of Genomic Research (Elshire R J et al. 2011. PLoS One 6:e19379). Using such a platform the marker detection and the scoring occur simultaneously and thousands of SNPs that passed through stringent quality control were detected. The SNPs were mapped using the genetic map construction tools of R/qtl that was developed and compiled by Karl W. Broman from the University of Wisconsin-Madison, Department of Biostatistics & Medical Informatics and described in Technical Report #214 (In: Broman K W and Sen S A. Guide to QTL Mapping with R/qtl. New York: Springer; 2009). A plot of estimated recombination fractions (upper-left triangle) and LOD scores (lower-right triangle) for all pairs of markers was generated (FIG. 5). Approximately 4500 markers yielded 69 linkage groups composed of markers where the longest distance between neighboring markers was fixed as being less than 20 percent recombination (FIG. 6). This cutoff was selected to prevent false unifications of linkage groups.

Example 4

Identification of QTL Conferring Vernalization Independence

Figure 7:
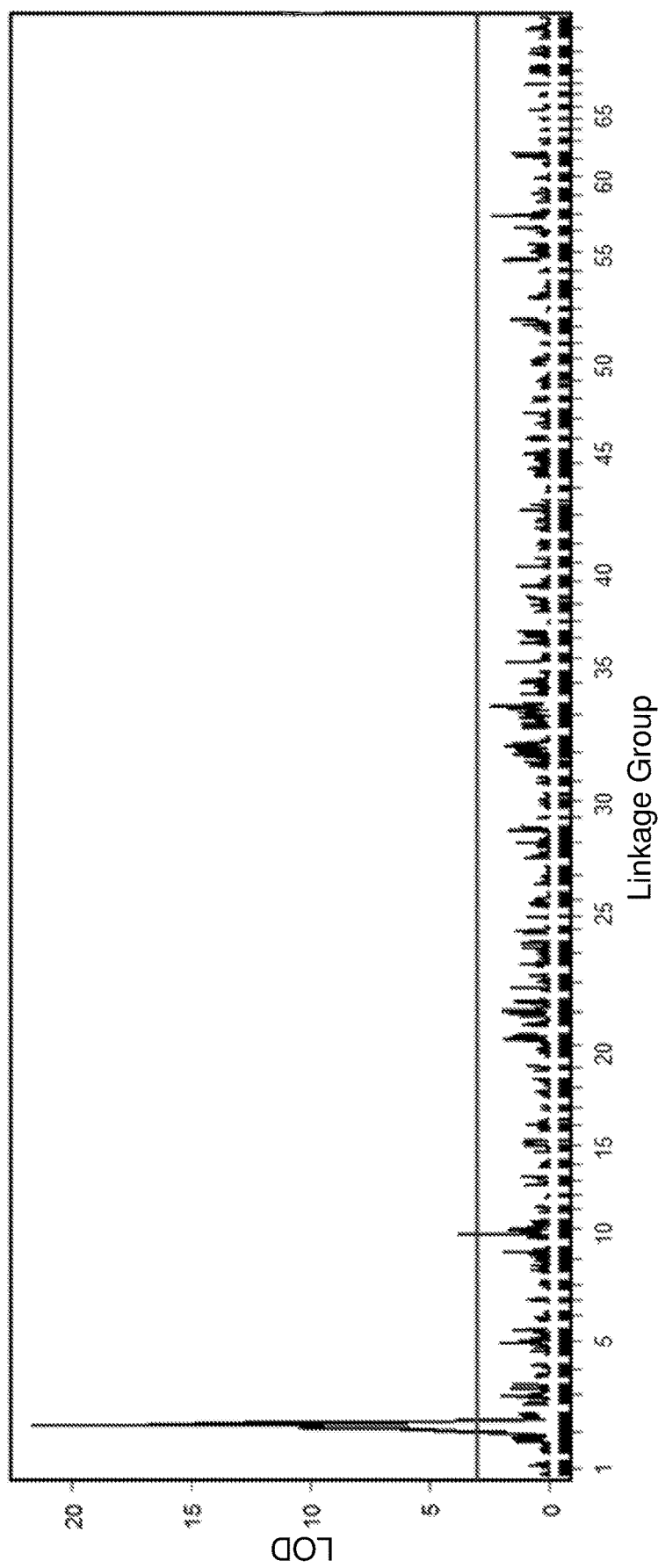
Figure 8:
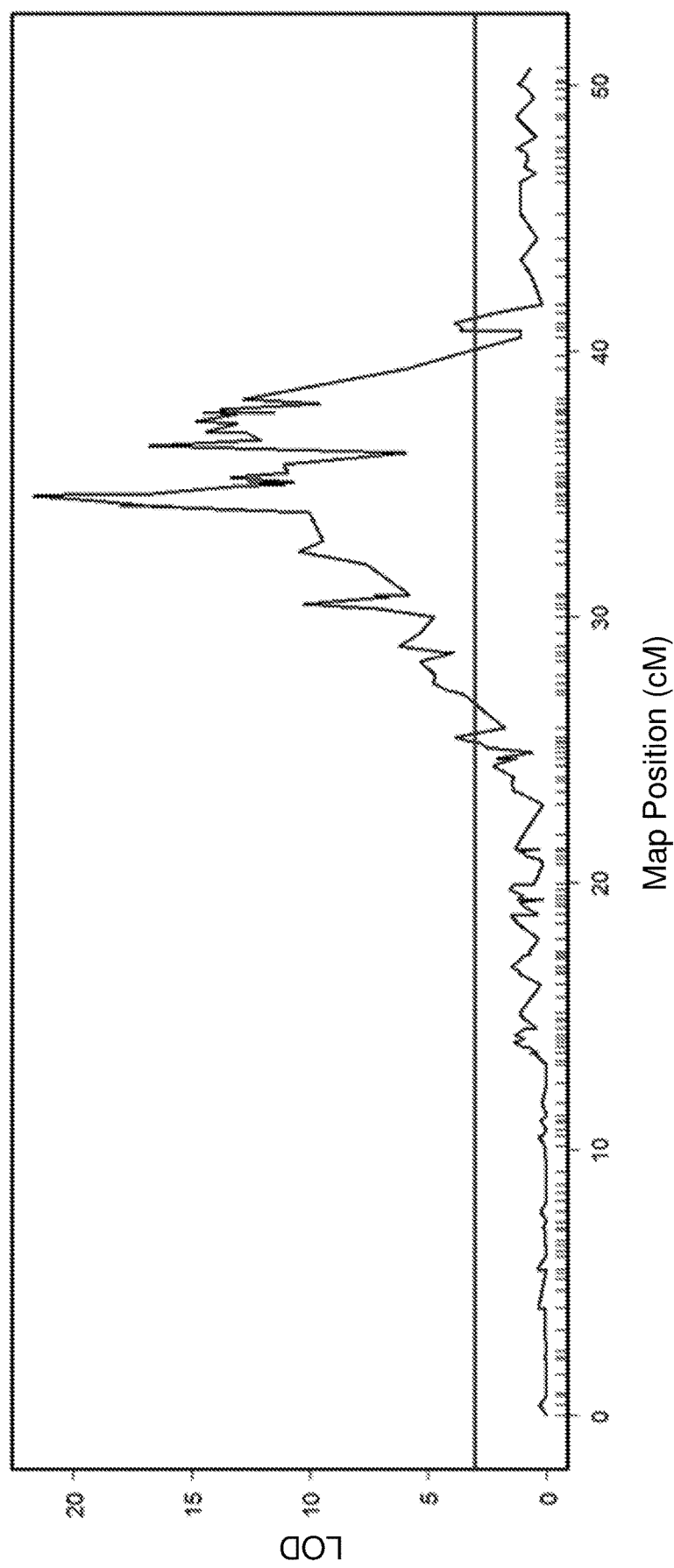

The QTL was identified using the bioinformatic capabilities of Phenome Networks (Rehovot, Israel) that developed a set of programs to display the details of different components of the complex phenotypes to uncover complex and hidden biological knowledge (Zamir D., 2013. PLoS Biol. 11: e1001595). Phenome Networks makes use of numerous R functions and algorithms that match the appropriate statistical models to the genetic structure of the populations. It is clear from FIG. 7 that a major QTL for vernalization (Lod 20) is located on linkage group 2 as was analyzed in the experiment in Shtil Neto in year 2013 based only on the homozygous RIs from both populations combined. A detailed view of Linkage group 2 (FIG. 8) shows that the QTL effect peeks in the interval between 30-40 cM on that linkage group.

Figure 9:
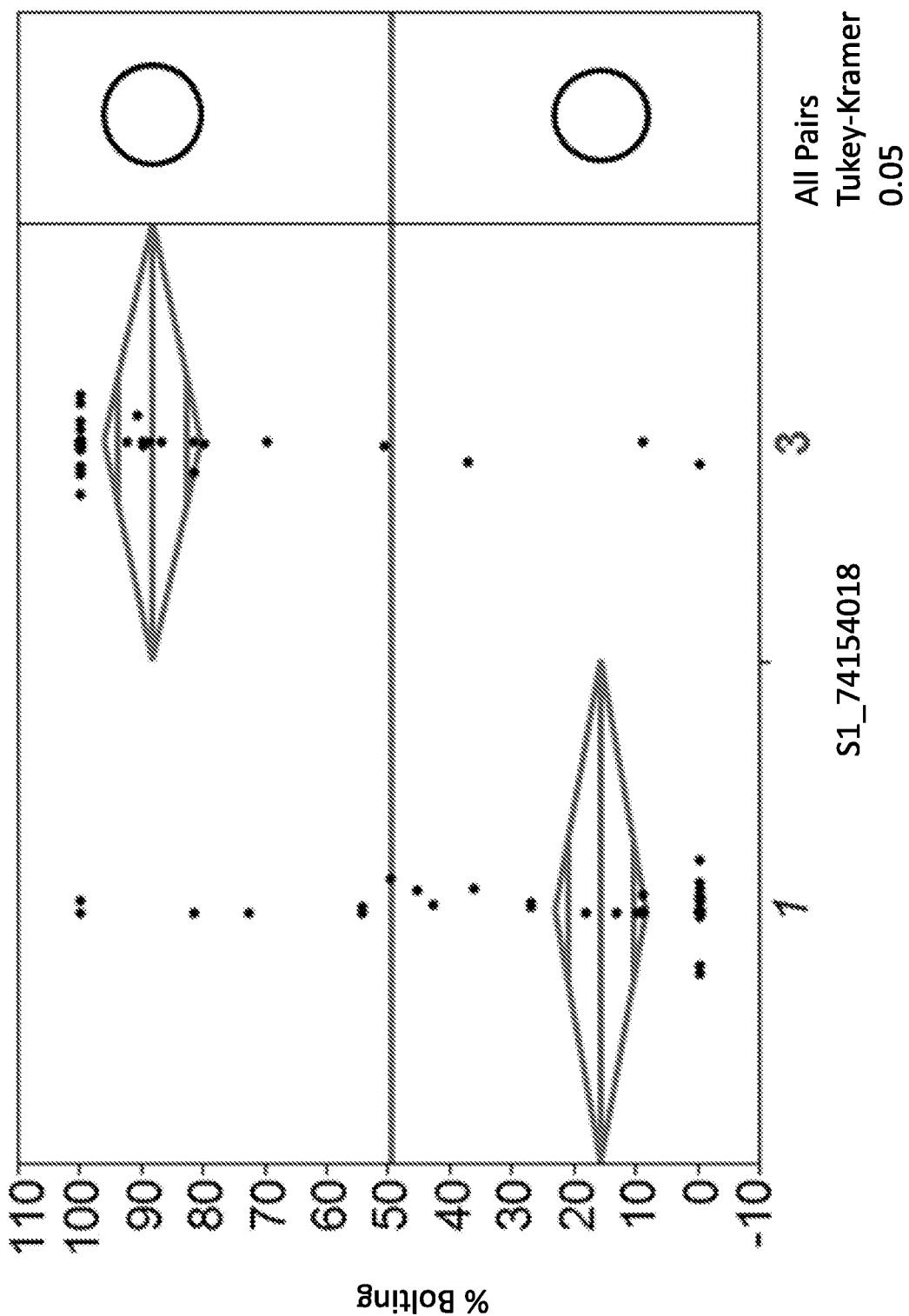

One of the strongest markers that affected the bolting phenotype was S1_74154018 (having the nucleic acid sequence set forth in SEQ ID NO:15). As presented in FIG. 9, in the group of plants with genotype 1 (homozygous for the E. grandiflorum allele) about 15% of the plant showed bolting and the rest of the 85% of the plants produced rosettes and did not flower, while in the group with genotype 3 (homozygous for the E. exaltatum allele) close to 90% of the plants bolted, supporting the position of the QTL on linkage group 2. Table 4 provides a summary of the bolting data from all the experiments which were conducted for the homozygous RIs showing the reproducibility of the effect. Similar results were obtained with markers located closer to the edges of the identified QTL, as presented in FIG. 15 for the genetic marker EG_0075 (having the nucleic acids sequence set forth in SEQ ID NO:3) located at position 30.5046992 and in FIG. 16 for the genetic marker S1_18474044 (having the nucleic acids sequence set forth in SEQ ID NO:40) located at position 38.2014392.

TABLE 4

Summary of Bolting Data for Homozygous *Eustoma* RIs relative to the marker S1_74154018

| Location | Population | Genotype 1 (No. of Plants) | Genotype 3 (No. of Plants) | % Bolting Genotype 1 (Mean) | % Bolting Genotype 3 (Mean) | F Ratio | Prob > F |
|---|---|---|---|---|---|---|---|
| ShtilNeto | P-RIL | 23 | 7 | 11.06 | 77.23 | 41.94 | <0.0001 |
| ShtilNeto | W-RIL | 25 | 35 | 20.66 | 90.9 | 104.3 | <0.0001 |
| ShtilNeto | P + W-RIL | 48 | 42 | 16.06 | 88.62 | 179.3 | <0.0001 |

P—Pink parent;
W—White parent;
RIL—Recombinant inbred line

Figure 10:
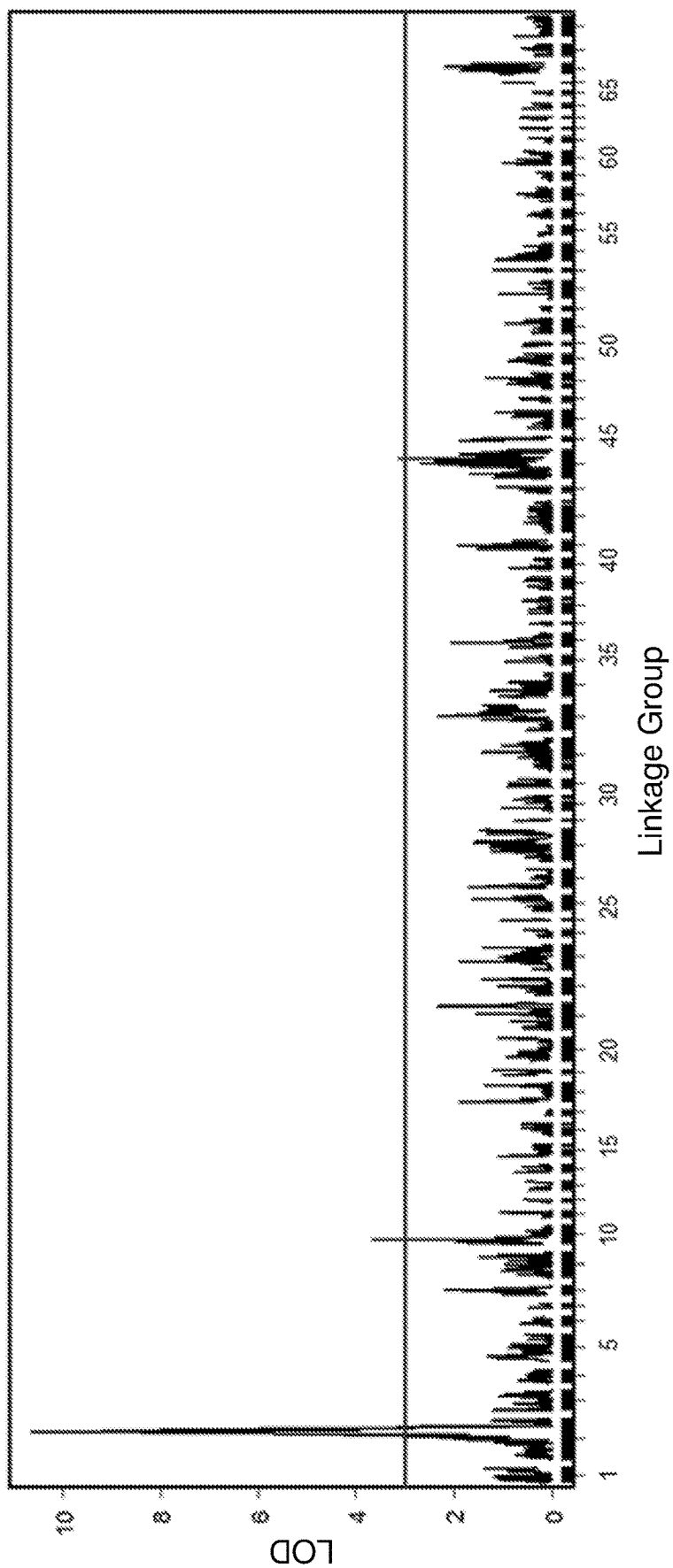
Figure 11:
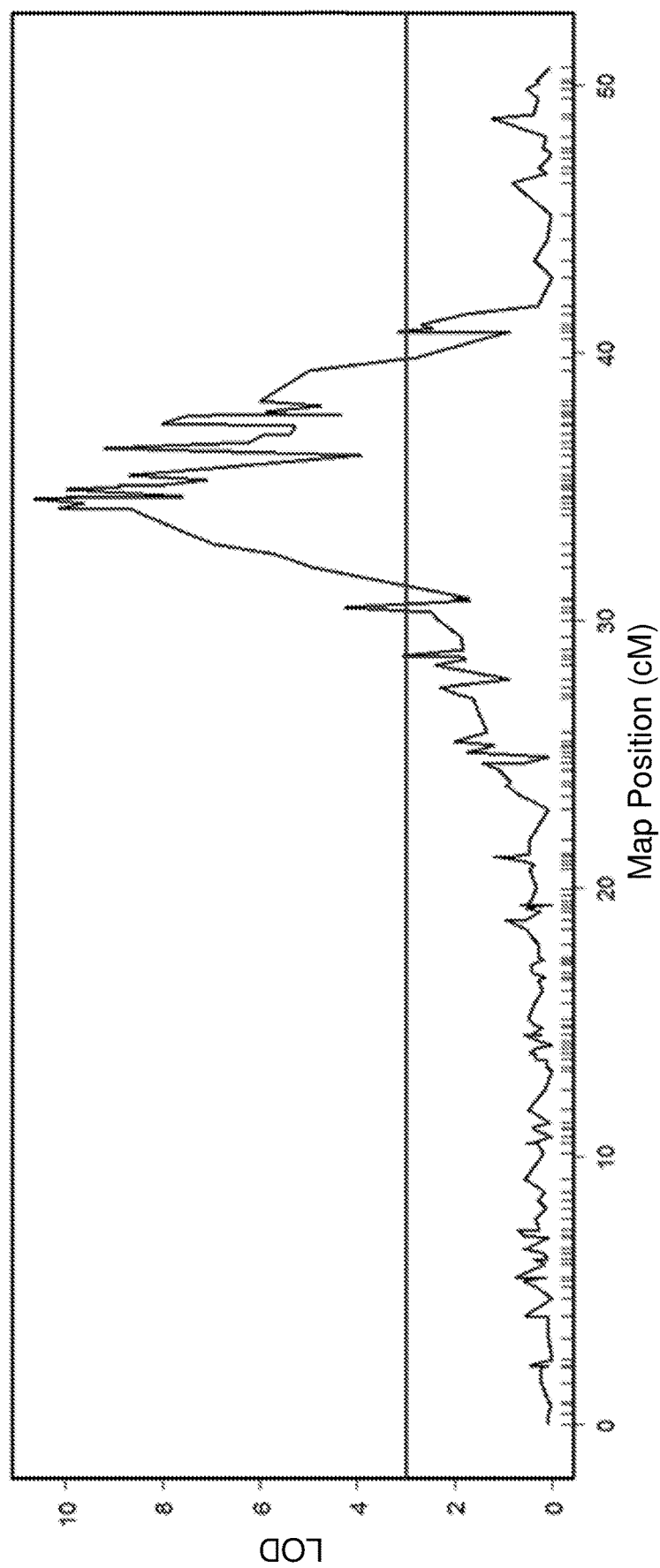
Figure 12:
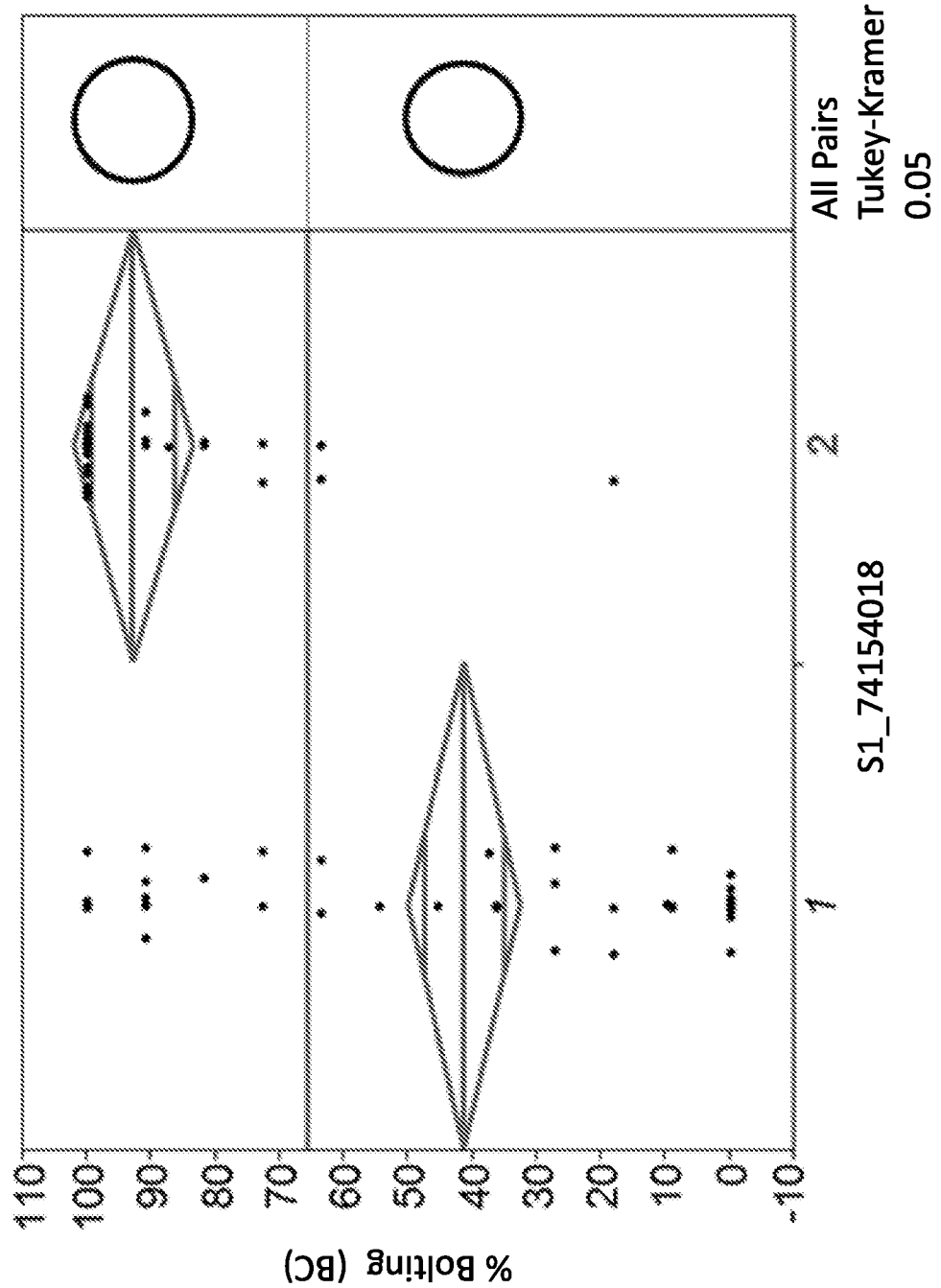

Unexpectedly, very similar observations linking the QTL to vernalization independence were found for the heterozygous RI hybrids. In this case seeds of the hybrids of the RIs with the respective *E. grandiflorum* parents were germinated. FIG. 10 shows that the major QTL for vernalization (Lod 20) is located on linkage group 2 as was shown for the homozygous population (FIG. 7), and the QTL effect peaked in the interval between 30-40 cM on that linkage group (FIG. 11). FIG. 12 shows that from the plants with genotype 1 (homozygous for the *E. grandiflorum* allele of S1_74154018) about 40% of the plant bolted and the rest 60% of the plants produced rosettes and did not flower, while in the group with genotype 2 (heterozygous plants comprising one *E. grandiflorum* allele and one *E. exaltatum* allele of S1_74154018) close to 90% of the plants bolted. Table 5 provides a summary of the bolting data from all the experiments conducted with heterozygous RIs showing the reproducibility of the effect.

These results clearly demonstrate that the QTL associated with insensitivity to vernalization is dominant, contrary to hitherto known vernalization-associated genes that were shown to be effective only when in homozygous state.

TABLE 5

Summary of Bolting Data for Heterozygous *Eustoma* RIs relative to the marker S1_74154018

| Location | Population | Genotype 1 (No. of Plants) | Genotype 2 (No. of Plants) | % Bolting Genotype 1 (Mean) | % Bolting Genotype 2 (Mean) | F Ratio | Prob > F |
|---|---|---|---|---|---|---|---|
| ShtilNeto | P-BC | 20 | 8 | 42.37 | 75 | 5.184 | 0.031 |
| ShtilNeto | W-BC | 26 | 33 | 40.91 | 97.42 | 63.08 | <0.0001 |
| ShtilNeto | P + W-BC | 46 | 41 | 41.54 | 93.04 | 64.53 | <0.0001 |

This finding was further confirmed by growing hybrid plants heterozygous for the *E. exaltatum* vernalization-independence allele (designated Flp) under high temperature conditions (day cycle of 12 h of 28° C. and 12 h of 34° C.) in a phytotron for three months. Leading commercial varieties (Rosita White, Rosita 2 Purple, Aube Pink Flush, Piccolo 2 Hot Lips, Rosita 3 Green, Eosita 3 Pink and Tzili) were used as control.

Figure 13A:
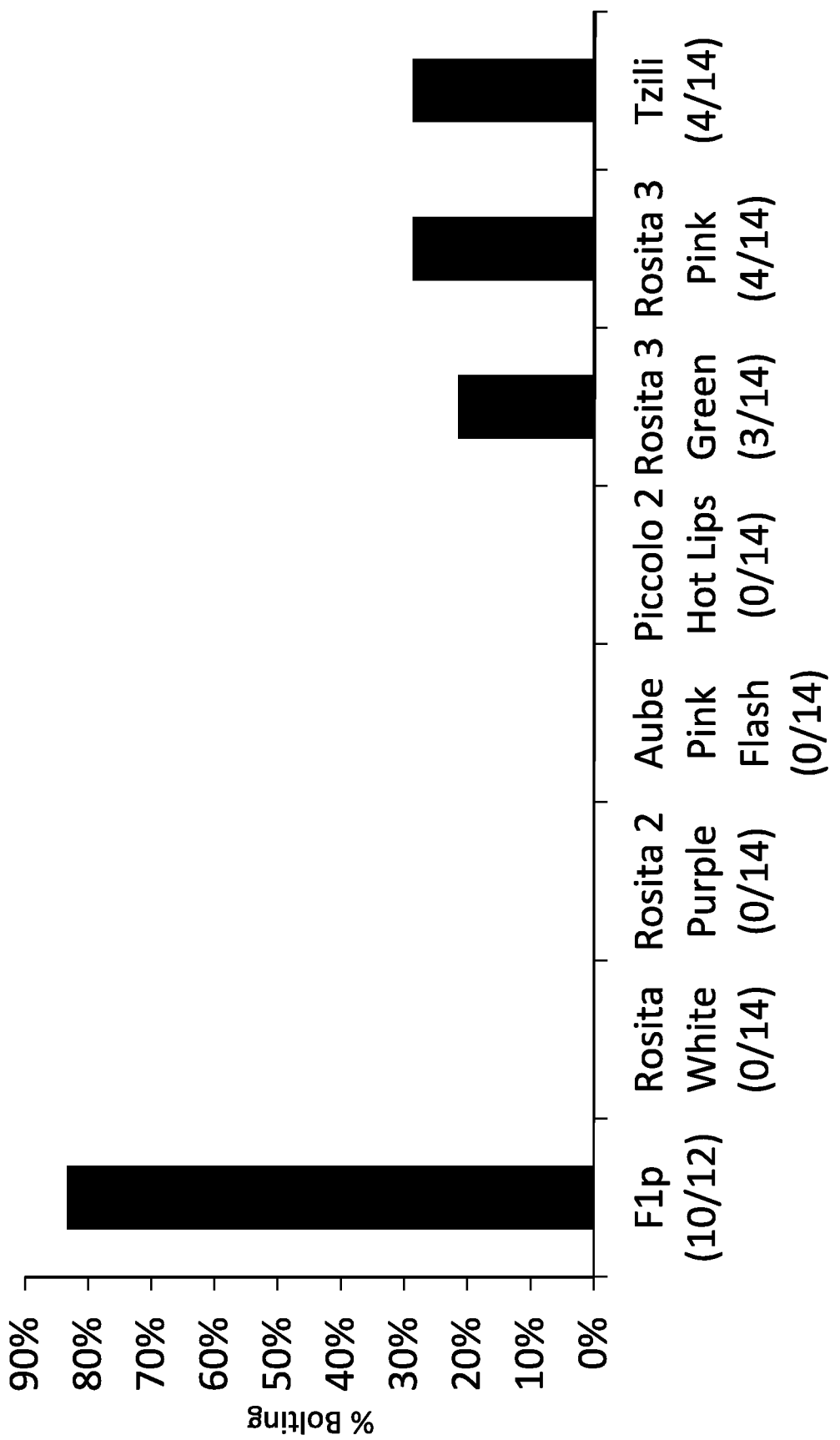
Figure 13C:
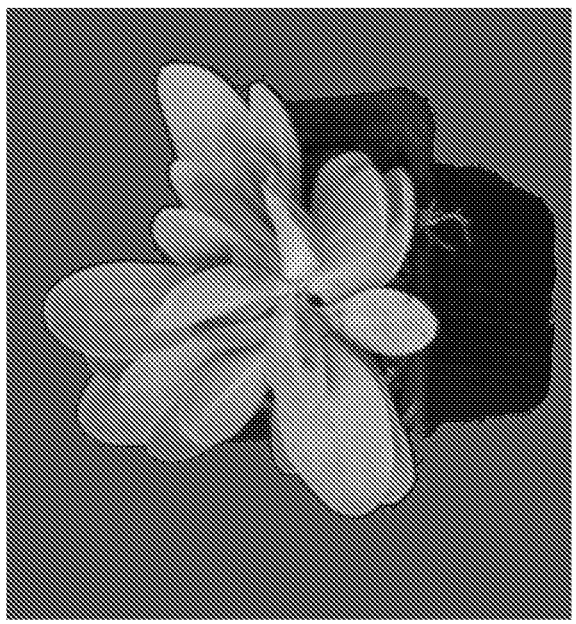
Figure 13B:
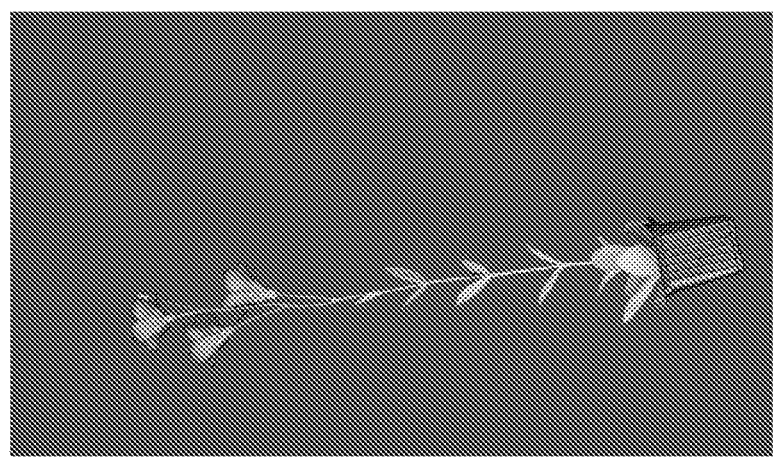

As is clearly shown in FIG. 13A, more than 80% of the heterozygous hybrid plant bolted compared to maxim of about 28% bolting in the vernalization-dependent varieties.

Example 5

Effect of the QTL Conferring Vernalization Independence on Additional Phenotypes Attempts to introgress beneficial traits from wild type or ancestor plants many times encounter the problem of significant genetic drag of undesirable traits from the donor into the receptor plant. However, not only that drag of undesired traits was negligible in the plants of the present invention, the QTL positively affected the number of stems in the second flowering flush typical to the growth pattern of lisianthus. FIG. 14 shows as average of 3.5 stems per plant in the second flush for plant of genotype 3 (homozygous for the *E. exaltatum* allele) compared to only 2.5 stems per plant in the second flush for plants having genotype 1 ((homozygous for the *E. grandiflorum* allele).

The QTL had a slightly negative effect on the pedicle length that slightly increased in plants comprising the QTL. Such increase is undesirable because it weakens the flowers that tend to break. However, this effect may be overcomes by introducing the QTL into lisianthus plants with appropriate genetic background of very short pedicles.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An ornamental *Eustoma grandiflorum* (*E. grandiflorum*) crop plant comprising a genetic element from linkage group 2 of *Eustoma exaltatum* (*E. exaltatum*) comprising a QTL, wherein the QTL comprises at least one marker located on the *E. exaltatum* linkage group 2 from about 25 cM to about 45 cM, wherein the at least one marker is selected from the group consisting of marker EG_0075 comprising the nucleic acid sequence set forth in SEQ ID NO:3; marker S1_74154018 comprising the nucleic acid sequence set forth in SEQ ID NO:15; and marker S1_18474044 comprising the nucleic acid sequence set forth in SEQ ID NO:40, and wherein the QTL confers vernalization independence to the ornamental *E. grandiflorum* crop plant.

2. The ornamental *E. grandiflorum* crop plant of claim 1, said plant bolts without receiving a cold treatment that is required for bolting in an ornamental *E. grandiflorum* crop plant devoid of said QTL or part thereof.

3. The ornamental *E. grandiflorum* crop plant of claim 1 wherein the QTL comprises at least one additional marker comprising the nucleic acid sequence set forth in any one of SEQ ID NOs:1-2, 4-14, 16-39 and 41-42.

4. The ornamental *E. grandiflorum* crop plant of claim 1, wherein the genetic element is located at a position from about 25 cM to about 45 cM on linkage group 2 of said ornamental *E. grandiflorum* crop plant.

5. The ornamental *E. grandiflorum* crop plant of claim 1, wherein the QTL further confers an increase in the number of flower stems during a second flowering flush compared to the stem number during the second flowering flush in a corresponding ornamental *E. grandiflorum* crop plant lacking the introduced QTL or parts thereof.

6. The ornamental *E. grandiflorum* crop plant of claim 1, said plant is devoid of deleterious genetic drags originated from the *E. exaltatum* linkage group 2.

7. A seed of the ornamental *E. grandiflorum* crop plant of claim 1, wherein a plant grown from the seed comprises a genetic element from linkage group 2 of *Eustoma exaltatum* comprising a QTL, wherein the QTL comprises at least one marker located on *E. exaltatum* linkage group 2 from about 25 cM to about 45 cM, wherein the at least one marker is selected from the group consisting of marker EG_0075 comprising the nucleic acid sequence set forth in SEQ ID NO:3; marker S1_74154018 comprising the nucleic acid sequence set forth in SEQ ID NO:15; and marker S1_18474044 comprising the nucleic acid sequence set forth in SEQ ID NO:40, and wherein the QTL confers vernalization independence to the plant.

8. A cell or a tissue culture obtained from the plant of claim 1, wherein a plant developed from the cell or tissue culture comprises a genetic element from linkage group 2 of *Eustoma exaltatum* comprising a QTL, wherein the QTL comprises at least one marker located on *E. exaltatum* linkage group 2 from about 25 cM to about 45 cM, wherein the at least one marker is selected from the group consisting of marker EG_0075 comprising the nucleic acid sequence set forth in SEQ ID NO:3; marker S1_74154018 comprising the nucleic acid sequence set forth in SEQ ID NO:15; and marker S1_18474044 comprising the nucleic acid sequence set forth in SEQ ID NO:40, and wherein the QTL confers vernalization independence to the plant.

9. A method for producing an ornamental *E. grandiflorum* crop plant independent on vernalization requirement for bolting, the method comprises introducing into an ornamental *E. grandiflorum* crop plant a genetic element from linkage group 2 of *Eustoma exaltatum* comprising a QTL, wherein the QTL comprises at least one marker located on *E. exaltatum* linkage group 2 from about 25 cM to about 45 cM, wherein the at least one marker is selected from the group consisting of marker EG_0075 comprising the nucleic acid sequence set forth in SEQ ID NO:3; marker S1_74154018 comprising the nucleic acid sequence set forth in SEQ ID NO:15; and marker S1_18474044 comprising the nucleic acid sequence set forth in SEQ ID NO:40, and wherein the QTL or part thereof confers vernalization independence to the ornamental *E. grandiflorum* crop plant, thereby producing ornamental *E. grandiflorum* crop plant independent on vernalization requirement for bolting and/or flowering.

10. The method of claim 9, wherein the QTL comprises at least one additional marker comprising the nucleic acid sequence set forth in any one of SEQ ID NOs:1-2, 4-14, 16-39 and 41-42.

* * * * *